US007892822B1

(12) United States Patent
Koszinowski et al.

(10) Patent No.: US 7,892,822 B1
(45) Date of Patent: Feb. 22, 2011

(54) RECOMBINANT VECTOR CONTAINING INFECTIOUS, VIRAL GENOME SEQUENCES GREATER THAN 100 KB, METHOD FOR PRODUCING SAME AND USE FOR THE MUTAGENESIS OF THE VIRAL SEQUENCES

(76) Inventors: Ulrich H. Koszinowski, Klementinenstrasse 14, D-80805 München (DE); Martin Messerle, Rudolfstrasse 4, D-82152 Planegg (DE); Wolfram Brune, Adlzreiterstrasse 13, D-80337 München (DE); Gabriele Hahn, Amalienstrasse 77, D-80799 München (DE)

( * ) Notice: Subject to any disclaimer, the term of this patent is extended or adjusted under 35 U.S.C. 154(b) by 0 days.

(21) Appl. No.: 09/463,890

(22) PCT Filed: Jul. 31, 1998

(86) PCT No.: PCT/EP98/04816

§ 371 (c)(1),
(2), (4) Date: Apr. 28, 2000

(87) PCT Pub. No.: WO99/06582

PCT Pub. Date: Feb. 11, 1999

(30) Foreign Application Priority Data

Aug. 1, 1997 (DE) ................................ 197 33 364

(51) Int. Cl.
C12N 15/70 (2006.01)
C12N 15/63 (2006.01)
C12N 5/00 (2006.01)
C12N 15/87 (2006.01)

(52) U.S. Cl. ..................... 435/320.1; 435/325; 435/463

(58) Field of Classification Search .............. 435/320.1, 435/91.4, 91.1, 6, 455, 471, 325, 243, 252.3; 536/23.1
See application file for complete search history.

(56) References Cited

U.S. PATENT DOCUMENTS 6,277,621 B1 * 8/2001 Horsburgh et al. ........ 435/235.1

FOREIGN PATENT DOCUMENTS

WO    WO96/15779    5/1996

OTHER PUBLICATIONS

Luckow, et al. Efficient Generation of Infectious Recombinant Baculoviruses by Site-Specific Transposon-Mediated Insertion of Foreign Genes into a Baculovirus Genome Propagated in *E. coli*. Journal of Virology. 1993, vol. 67, No. 8, pp. 4566-4579.*
Kempkes, et al. Immortalization of Human Primary B Lymphocytes In Vitro with DNA. Proceedings of the National Academy of Sciences, USA. Jun. 1995, vol. 92, pp. 5875-5879.*
Delecluse, et al. Propagation and Recovery of Intact, Infectious Epstein-Barr Virus from Prokaryotic to Human Cells. Proceedings of the National Academy of Sciences, USA. Jul. 7, 1998, vol. 95, pp. 8245-8250.*
Stavropoulos, et al. An enhanced Packaging System for Helper-Dependent Herpes Simplex Virus Vectors. Journal of Virology. Sep. 1998, vol. 72, No. 9, pp. 7137-7143.*
Saeki, et al. Herpes Simplex Virus Type I DNA Amplified as Bacterial Artificial Chromosome in *Escherichia coli*: Rescue of Replication-Competent Virus Progeny and Packaging of Amplicon Vectors. Human Gene Therapy. Dec. 10, 1998, vol. 9, pp. 2787-2794.*
Smith, et al. A Self-Replicating Bacterial Artificial Chromosome and Its Application for Analysis of Herpesviral Pathogenesis. Proceedings of the National Academy of Sciences, USA. 2000, vol. 97, No. 9, pp. 4873-4878.*
Suter, et al. BAC-VAC, a Novel Generation of (DNA) Vaccines: A Bacterial Artificial Chromosome (BAC) Containing a Replication-Competent, Packaging-Defective Virus Genome. PNAS USA. Oct. 1999, vol. 96, No. 22, pp. 12697-12702.*
Borst, et al. Cloning of the Human Cytomegalovirus (HCMV) Genome as an Infectious Bacterial Artificial Chromosme in *E. coli*: a New Approach for Construction of HCMV Mutants. Journal of Virology, Oct. 1999, vol. 73, No. 10, pp. 8320-8329.*
Almazan, et al. Engineering the Largest RNA Virus Genome as an Infectious Bacterial Artificial Chromosome. Proceedings of the National Academy of Sciences, USA. May 2000, vol. 97, No. 10, pp. 5516-5521.*
Domi, et al. Cloning the Vaccinia Virus Genome as a Bacterial Artificial Chromosome in *E. coli* and Recovery of Infectious Virus in Mammalian Cells. Proceedings of the National Academy of Sciences, USA. Sep. 2002, vol. 99, No. 19, pp. 12415-12420.*
Yu, et al. Construction of Self-Excisable Bacterial Artificial Chromosome Containing the Human Cytomegalovirus Genome and Mutagenesis of the Diploid TRL/IRL 13 Gene. Journal of Virology. Mar. 2002, vol. 76, No. 5, pp. 2316-2328.*
Mahony, et al. Construction and Manipulation of an Infectious Clone of the Bovine Herpesvirus 1 Genome Maintained as a Bacterial Artificial Chromosome. Journal of Virology. Jul. 2002, vol. 76, No. 13, pp. 6660-6668.*
Warnes et al. (1986) Plasmid 16:116-123.*
Tomkinson et al. (1993) J. Virol. 67:7298-7306.*
Ehtisham et al. (1993) J. Virol. 67:5247-5252.*
Gage et al. (1992) J. Virol. 66:5509-5515.*
Roizman et al. (1985) Science 229:1208-1214.*
Chen et al. (1987) Mol. Cell. Biol. 7:2745-2752.*
Chartier et al. J. Virol. 70:4805-4810; 1996.*
Kong et al. J. Virol. Methods 80:129-136; 1999.*
Kemble et al. J. Virol. 70:2044-2048; 1996.*
Gage et al., "A Cell-Free Recombination System for Site-Specific Integration of Multigenic Shuttle Plasmids into the Herpes Simplex Virus Type 1 Genome," *J. of Virology*, vol. 66, No. 9, pp. 5509-5515 (1992).

(Continued)

*Primary Examiner*—Michael Burkhart
(74) *Attorney, Agent, or Firm*—Leydig, Voit & Mayer, Ltd.

(57) ABSTRACT

Recombinant vectors containing infectious viral genomic sequences as well as sequences of a cloning vehicle, a cell comprising the vector, a method for producing the vectors, a method of mutagenizing an infectious viral genomic sequence in the vector, and a vector obtained by the method.

33 Claims, 25 Drawing Sheets

OTHER PUBLICATIONS

Ketner et al., "Efficient Manipulation of the Human Adenovirus Genome as an Infectious Yeast Artificial Chromosome Clone," *Proc. Nat'l. Acad. Aci. USA*, vol. 91, pp. 6186-6190 (1994).

Messerle et al., "Cloning and Mutagenesis of a Herpes Virus Genome as an Infectious Bacterial Artificial Chromosome," *Proceeding of the National Academy of Sciences of USA*, vol. 94, No. 26, pp. 14759-14763 (1997).

Messerle et al., "Reconstitution of a Recombinant Cytomegalo Virus from Two Fragments Cloned into Bacterial Artificial Chromosomes; Mouse Cytomegalo Virus Genome Cloning in *Escherichia coli* Bacterial Artificial Chromosome for Use as a Vector in Gene Therapy," *Journal of Molecular Medicine*, vol. 74, No. 4, p. B8 (1996).

Shizuya et al., "Cloning and Stable Maintenance of 300-Kilobase-Pair Fragments of Human DNA in *Escherichia coli* Using an F-Factor-Based Vector," *Proceedings of the National Academy of Sciences of USA*, vol. 89, pp. 8794-8797 (1992).

Spaete et al., "Insertion and Deletion Mutagenesis of the Human Cytomegalievirus Genome," *Proc. Nat'l. Acad. Sci. USA*, vol. 84, pp. 7213-7217 (1987).

Brune et al., "Forward with BACs: new tools for herpesvirus genomics," TIG, vol. 16, No. 6, pp. 254-259 (2000).

Muyrers et al., "ET Recombination: DNA Engineering Using Homologous Recombination in *E. coli*," Methods in Molecular Biology, vol. 256, pp. 107-121 (2004).

Ruzsics et al., "Transposon-Assisted Cloning and Traceless Mutagenesis of Adenoviruses: Development of a Novel Vector Based on Species D," Journal of Virology, vol. 80, No. 16, pp. 8100-8113 (2006).

Ruzsics and Koszinowski, "Mutagenesis of the Cytomegalovirus Genome," In: *Human Cytomegalovirus*, T.E.Shenk and M.F.Stinski, eds. Berlin, Heidelberg: Springer, pp. 41-61 (2008).

Sirena et al., "The nucleotide sequence and a first generation gene transfer vector of species B human adenovirus serotype 3," Virology, Issue 343, pp. 283-298 (2005).

Warming et al., "Simple and highly efficient BAC recombineering using *galK* selection," Nucleic Acids Research, vol. 33, No. 4 (2005). 12 pgs.

Zhang et al., "DNA cloning by homologous recombination in *Escherichia coli*," Nature Biotechnology, vol. 18, pp. 1314-1317 (2000).

* cited by examiner

Fig. 21
a
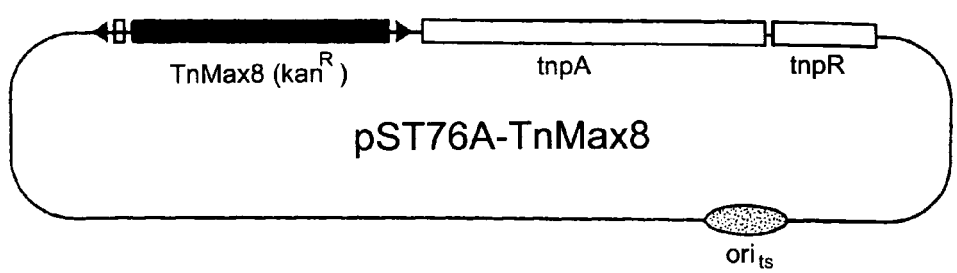
b
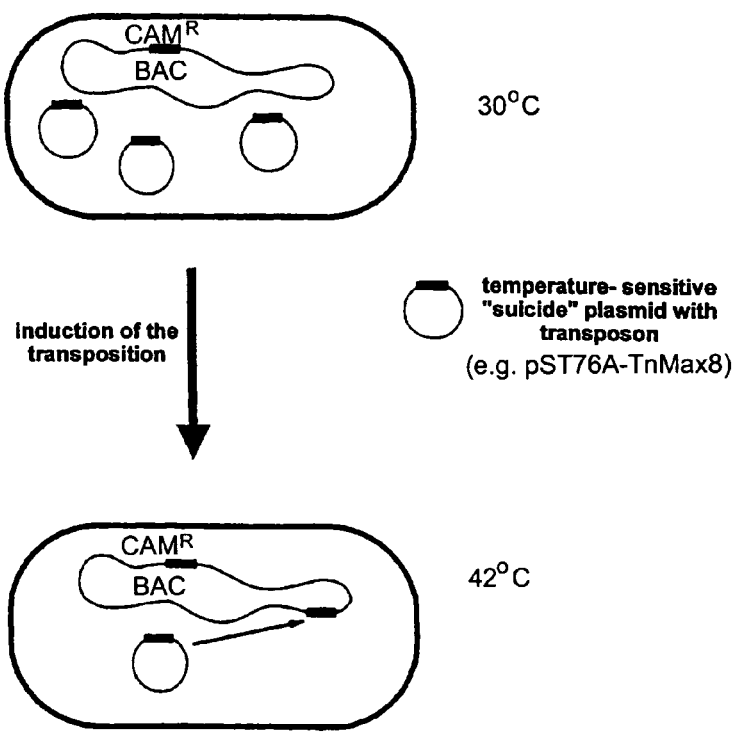

SEQUENCE LISTING

<160> NUMBER OF SEQ ID NOS: 2

<210> SEQ ID NO 1
<211> LENGTH: 60
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (25)..(25)
<223> OTHER INFORMATION: n is any nucleotide
<220> FEATURE:
<221> NAME/KEY: misc_feature
<222> LOCATION: (27)..(27)
<223> OTHER INFORMATION: n is any nucleotide
<220> FEATURE:
<221> NAME/KEY: misc_feature
<222> LOCATION: (37)..(37)
<223> OTHER INFORMATION: n is any nucleotide
<220> FEATURE:
<221> NAME/KEY: misc_feature
<222> LOCATION: (52)..(52)
<223> OTHER INFORMATION: n is any nucleotide

<400> SEQUENCE: 1
ggagatcccg aaacggccga gctcntncag gttgcgngcc accaggtgca gngtgtcgtc    60

<210> SEQ ID NO 2
<211> LENGTH: 60
<212> TYPE: DNA
<213> ORGANISM: Artificial
<220> FEATURE:
<223> OTHER INFORMATION: Synthetic

<400> SEQUENCE: 2
ggagatcccg aaacggccga gctcctccag gttgcgcgcc accaggtgca gcgtgtcgtc    60

RECOMBINANT VECTOR CONTAINING INFECTIOUS, VIRAL GENOME SEQUENCES GREATER THAN 100 KB, METHOD FOR PRODUCING SAME AND USE FOR THE MUTAGENESIS OF THE VIRAL SEQUENCES

The present invention relates to recombinant vectors containing infectious viral genome sequences as well as sequences of a cloning vehicle, and to a method for producing said vectors. Furthermore, the present invention relates to the use of such recombinant vectors, especially for the mutagenesis of the infectious viral genome sequences contained therein, and to a method for the mutagenesis of said sequences.

Various viruses with a large DNA are important pathogens, either for human beings or for animals or plants, partly causing severe or even fatal diseases. Reference is made by way of example to the cytomegalovirus (CMV) which is counted among the most important human pathogenic viruses. CMV has a high prevalence in the human population and can cause severe diseases, especially in immunologically immature patients or in immunocompromised patients (1). Since human cytomegalovirus (CMV) and mouse cytomegaloviurs (MCMV) show several similarities in their biology and pathogenesis (2), infection of mice with MCMV has become an intensively examined in vivo model to study the pathogenesis of CMV infection. The approximately 235 kb large genomes of both human and mouse CMV are the largest genomes of mammalian DNA viruses. Sequence analysis of the human and mouse CMV genomes reveal a similar genetic organization and a coding capacity for presumably more than 220 polypeptides (3, 4, 5).

The size of the genome of such viruses makes it difficult to clone and analyze the whole genome or the parts of the genome required for replication and packaging, and to make targeted changes. This is inter alia due to the fact that the methods which have been used up to now rely on the use of multiple recombination steps in eukaryotic cells which are firstly rare, secondly prone to errors and thirdly cannot be controlled in practice. This requires troublesome selection methods for isolating and characterizing the desired mutants.

Information on the function of a majority of CMV gene products is still rather limited because of the size of the viral DNA and the associated difficult manipulatability of the viral genome, and until now it has been very difficult to obtain CMV clones and CMV mutants because of their large DNA and their slow replication kinetics. This is e.g. in contrast to the situation regarding the herpes simplex virus (α-herpesviruses) (6) which has been studied in detail and for which the function of many viral genes could be elucidated.

A method for insertional mutagenesis in eukaryotic cells has been developed for the disruption and deletion of CMV genes (7, 8). However, since the frequency of homologous recombinations in eukarytoic cells is low, the method is quite ineffective. In addition adventitious deletions and the production of undesired recombinant viruses have frequently been observed (7, 9). Although selection procedures have improved the original method (9, 10, 11), generation of CMV mutants remains a laborious and often unsuccessful task. Recently, a method for constructing recombinant herpesviruses from cloned overlapping fragments (12) has been applied to CMV (13). This is a major improvement in comparison with the above-described methods in that said method generates only recombinant viruses and obviates selection against non-recombinant wild-type viruses. Still; the resultant mutants are the product of several recombination events in eukaryotic cells that are difficult to control. Correct reconstitution of the viral genome can only be verified after growth and isolation of the viral mutant.

It is the object of the present invention to provide recombinant vectors which make it possible to introduce the complete genome, or at least those parts of the genome of a virus that are required for replication and packaging, with the genome of the virus being larger than 100 kb, preferably larger than 200 kb, into an organism or cell and to maintain and multiply the same there, and to perform targeted changes in the viral sequences.

Said object is achieved by a recombinant vector which contains infectious viral genome sequences having a size larger than 100 kb, preferably larger than 200 kb, as well as sequences of a cloning vehicle. The expression "infectious viral genome sequences" within the meaning of the invention covers both the complete genome and those parts of the genome of a virus that are indispensable for replication and packaging in a host organism or host cell.

The infectious viral genome sequences of the recombinant vector according to the invention can derive from a DNA virus; preferably, they derive from a herpesvirus, and particular mention should here be made of the human cytomegalovirus (an important pathogen for humans) and the mouse cytomegalovirus. Furthermore, genome sequences from other DNA viruses and all herpesvirus genomes are suited, for instance herpes simplex virus type 1 (size of the genome: 152 kb) and 2 (155 kb), Epstein-Barr virus (172 kb), varicella-zoster virus (125 kb), human herpesviruses 6, 7 or 8 (HHV6, 159 kb; HHV7, 145 kb; HHV8, about 160 kb), animal herpesviruses, e.g. pseudorabies virus (about 130 kb), bovine herpesviruses 1 (135 kb), 2 (140 kb), 3 or 4 (156 kg), and the murine gammaherpesvirus 68 (MHV 68, about 140 kb).

The sequences of a cloning vehicle which are contained in the recombinant vector according to the invention are capable to replicate in suited host cells or organisms and serve as carriers for the viral sequences which are passively co-replicated and can be isolated and purified together with the sequences of the cloning vehicle. It has been found that a low copy number of the recombinant vector of the invention in the host cell is of advantage to the stability of the viral genome sequences contained therein. Therefore, sequences of a cloning vehicle that derive from low-copy vectors are preferred. In a preferred embodiment of the invention these sequences derive from the known mini-F plasmids of E. coli.

In a particularly preferred embodiment of the recombinant vector of the invention, the vector is formed as an artificial circular chromosome, preferably as a bacterial artificial chromosome (BAC), or also as a yeast artificial chromose (YAC).

Since according to the invention the recombinant vector of the invention contains infectious genome sequences, it can be replicated and packaged like a viral genome after introduction into a suitable permissive cell. However, it has been found that the packaging of the virus particles is impaired by the overlength of the vector (as compared to the original length of the viral genome sequences) which is due to the presence of sequences of a cloning vehicle. Therefore, it is advantageous to remove the sequences of the cloning vehicle from the recombinant vector prior to replication and packaging of the viral genome sequences. To this end, in one embodiment of the invention, the sequences of the cloning vehicle are flanked by identical sequence sections which make it possible to excise the sequences by homologous recombination.

In a further, particularly preferred embodiment of the vector according to the invention, the sequences of the cloning vehicle are flanked by recognition sequences for sequence-specific recombinases and/or restriction sites which do not occur in the rest of the vector. To obtain infectious viral genome sequences that are free from sequences of the cloning vehicle, these are excised by a recombinase, e.g. by the recombinase FLP, and/or by a restriction enzyme. Particularly preferred are recombinant vectors in which the recognition sequences for sequence-specific recombinases are loxP sites which are recognized and cut by the recombinase Cre. Optionally, the viral genome sequences to be cloned can first be introduced into a suitable cell if the cell containing the same is not suited for cloning.

Preferably, the vector according to the invention contains selection and/or marker genes, for instance gpt, the hygromycin resistance gene, the neomycin resistance gene, the green-fluorescent protein or the lacZ gene, to facilitate the selection (enrichment) and identification (e.g. by staining techniques) of cells containing recombinant vectors.

The present invention also relates to cells which contain a recombinant vector of the above-described type.

Furthermore, it is the object of the present invention to provide a method for producing a recombinant vector of the invention which allows the cloning of large, if possible complete, but at any rate infectious (i.e. replication-capable), viral genome sequences in eukaryotic cells with the number of recombination steps being as low as possible, and which does not call for a repeated isolation and selection of the recombinants.

According to the present invention this object is achieved by a method comprising the following steps:

a) introducing a sequence (1) containing sequences of a cloning vehicle, into a cell containing infectious viral genome sequences, and b) recombining sequence (1) of step a) with the viral genome sequences, preferably via homologous recombination, to obtain a recombinant vector.

The method is particularly suited for cloning those genome sequences that are larger than 100 kb (preferably larger than 200 kb), but it can also be used for cloning smaller DNA fragments. Examples of viral genome sequences that can be recombined according to the method of the invention with sequence (1) include the genomes of the herpes simplex virus type 1 (size of the genome: 152 kb) and type 2 (155 kb), the Epstein-Barr virus (172 kb), the varicella-zoster virus (125 kb), the human herpesviruses 6, 7 or 8 (HHV6, 159 kb; HHV7, 145 kb; HHV8, about 160 kb), animal herpesviruses, such as pseudorabies virus (about 130 kb), bovine herpesviruses 1 (135 kb), 2 (140 kb), 3 or 4 (156 kb), and the murine gammaherpesvirus 68 (MHV 68, about 140 kb). The homologous recombination between the viral sequences and sequence (1) can e.g. be achieved when sequence (1) contains sections that are homologous to the viral genome sequences to be cloned.

Preferably, eukaryotic cells, such as mammalian cells, insect cells or yeast cells, are used as host cells for step a); human primary fibroblasts (e.g. human foreskin fibroblasts (HFF)), NIH3T3 fibroblasts (ATCC CRL1658), or mouse fibroblasts can here in particular be used. For the introduction of sequence (1), hosts cells are selected that are permissive for the respective virus, i.e. cells which are able to support the growth of said virus. The introduction of sequence (1) into eukaryotic cells is carried out by a calcium phosphate precipitation method, an electroporation method or a lipofection method or by means of other methods of the latest prior art. Sequence (1) can also be introduced into the cell by a viral vector.

In a particularly preferred embodiment of the production method according to the invention, a bacterial organism, preferably E. coli, is used as the cell in step a). Sequence (1) can e.g. be introduced by electroporation or by any other method known in the prior art.

Furthermore, the invention relates to the use of a recombinant vector of the above-described type for the mutagenesis of the infectious viral genome sequences contained therein.

It is a further object of the present invention to provide a method by which modifications can be made in the viral genome sequences contained in the vector of the invention.

This object is achieved by a mutagenesis method comprising the following steps:

A) introducing the recombinant vector into a bacterial host cell or into yeast; and mutagenizing the viral genome sequences.

Mutagenesis can be carried out either in a targeted manner by homologous recombination with DNA molecules carrying the mutation that are contained in the bacterial host cell or yeast (e.g. as shuttle plasmid), or at random, e.g. by transposon mutagenesis. "Mutagenesis" in the sense of the present invention means the introduction of any possible modification in the genetic material, e.g. deletions, insertions, substitutions or point mutations.

The mutagenesis method according to the invention is advantageous in that the modifications in the bacterial host cell or in yeast take place without any selection pressure. Thus, mutations can also be introduced into the genome that may entail a growth disadvantage (or even a letal phenotype) for the mutant. With the former mutagenesis methods for herpesviruses, this is either not at all possible or only possible under considerable efforts. During mutagenesis attention need first not be paid to the later characteristics of the viral mutant because the production of the mutant genome and the production and characterization of the viral mutant are separate processes.

A transposon mutagenesis of cloned herpesvirus genomes is useful for a simple and efficient production of a great number of mutants that may inter alia serve screening methods. An extensive library with mutations in all genes and in all regulatory sequences can be generated by a saturating mutagenesis.

In an advantageous embodiment of the mutagenesis method of the invention, the recombinant vector is obtainable according to one of the above-described production methods.

Furthermore, the invention relates to a recombinant vector which contains infectious viral genome sequences modified by a mutagenesis method as described above, which have a size larger than 100 kb, preferably larger than 200 kb, as well as sequences of a cloning vector.

The introduction of the mutagenized vector into permissive cells exclusively results in the formation of uniform viral mutants because the introduced vectors are clonal, i.e., they can be traced back to a bacterial cell (clone) or to a vector molecule. Subsequent selection or enrichment methods for mutants which are troublesome and time-consuming as a rule—typically part of former mutagenesis methods for large virals genomes—are therefore not necessary.

Both mutagenized and non-mutagenized recombinant vectors according to the invention are suited as drugs, preferably for performing somatic gene therapy, or as a vaccine.

The following uses are possible for the vectors and methods according to the invention:

Characterization of viral genes or functions and viral proteins, for instance with the aim to identify essential viral structures, in order to develop inhibitors (drugs) against viruses.

Production of a CMV vaccine or CMV-based vaccines against other pathogens (attenuation of the virus by deletion of genes, or insertion of genes coding for antigens).

Production of vectors for gene therapy (deletion of viral genes, replacement by therapeutically useful transgenes).

The attached drawings shall now be described:

FIG. 1 shows a strategy for the cloning and mutagenesis of a large viral genome using the production and mutagenesis methods according to the invention.

(A) A large viral genome and a recombination plasmid with bacterial vector sequences were introduced into eukaryotic cells to generate a recombinant DNA (BAC). This can be performed by various methods, e.g. infection, transfection, electroporation, etc. Circular DNA was isolated from the infected cells and transferred into E. coli. (B) Mutagenesis of the BAC was performed in E. coli by homologous recombination with a mutant allele, and the mutated BAC was transfected into eukaryotic cells to reconstitute recombinant viral genomes or viruses (C).

FIG. 2 shows the construction and structure of the MCMV bacterial artificial chromosomes (BACs) pSM3 (a) and pSM4 (b) and the genome structure of the derived recombinant viruses MC96.73 and MC96.74. The EcoRI restriction map of the right-terminal end of the genome of the MCMV strain Smith is shown above. The recombinant plasmids pRP2 and pRP3 contain 2.2 and 6.6 kb of flanking MCMV homologous sequences (white boxes), the BAC vector (grey) and the gpt gene (hatched), flanked by loxP sites (black). The EcoRI restriction map of the BACs pSM3 and pSM4 is shown thereunder. The terminal EcoRI fragments of the MCMV genome are fused into the BAC plasmids pSM3 and pSM4, resulting in new fragments of 22.9 and 24.3 kb, respectively. The linear genomes of the recombinant viruses MC96.73 and MC96.74 contain terminal EcoRI fragments of a length of 12.3 and 13.7 kb, respectively. Additional restriction sites are indicated by BamHI (B), HindIII (H) and SfiI (S).

FIG. 3 shows the structural analysis of the bacterial artificial chromosomes (BACs) pSM3 and pSM4 (a) and the reconstituted viral genomes (b, c). (a) Ethidium bromide-stained agarose gel of EcoRI-digested BACs isolated from E. coli cultures (lanes pSM3 and pSM4) and of wild-type MCMV DNA isolated from purified virions (lane wt). (b) Restriction enzyme analysis of the viral MC96.73 and MC96.74 genomes. The BACs pSM3 and pSM4 were transfected into mouse embryonic fibroblasts and the supernatant of the transfected cells was used for infecting new cells. The DNA isolated from the infected cells and wild-type MCMV DNA were digested with EcoRI and separated by electrophoresis on 0.6% agarose gels for 14 hours. The EcoRI O(O) and the vector fragments (v) are indicated and the size of the additional bands is shown at the left side. (c) Separation of the EcoRI fragments shown in (b) after electrophoresis for 28 hours.

FIG. 4 shows the construction of the MCMV IE1 mutant MM96.01 (a), the structural analysis of the mutated bacterial artificial chromosome, (BAC) (b) and the genome of the IE1 mutant MM96.01 (c). The HindIII site between the HindIII K and L fragments of the genome of the MCMV strain Smith (top) was removed by mutagenesis using the EcoRI/HpaI fragment (hatched region). The exon-intron structure of the IE1 and IE3 genes is indicated, and the protein-coding sequences are depicted as hatched boxes. The mutation results in a frame shift after 273 codons and in the formation of a new stop codon after another 9 codons (black box). The open box denotes the part of the IE1 open reading frame which is not translated in the mutated virus. (b) Ethidium bromide-stained agarose gel of the HindIII-digested parental BAC pSM3 and of the mutated BAC pSMIE1. (c) HindIII pattern of the genomes of recombinant virus MC96.73 and of the IE1 mutant MM96.01. The HindIII K and L fragments and the new 15.2-kb fragment are indicated at the left side and the size of some HindIII fragments is shown at the right margin.

FIG. 5 shows the absence of pp 89 in cells infected with the IE1 mutant MM96.01. Mouse embryonic fibroblasts (MEF) were either not infected, infected with the recombinant virus MC96.73 or with the IE1 mutant MM96.01 in the presence of cycloheximide (50 µg/ml) for 3 hours for achieving a selective expression of the immediate-early proteins (16). After removal of cycloheximide, actinomycin D (5 µg/ml) was added and the proteins were labeled with [$^{35}$S]-methionine (1200 ci/mmol) for 3 additional hours. Lysis of cells and immunoprecipitations were performed as described (28) using antiserum 3/1 directed to the C-terminus of the IE1 protein pp 89 (a) and the IE1/IE2-specific antipeptide serum b5-1 (b) (16, 28). A long exposure of the autoradiograph (b) is shown in (c).

FIG. 6 shows a strategy for the reconstitution of the complete MCMV genome in E. coli and excision of the vector sequences after transfection of permissive cells with the MCMV BAC vector, as described in Example 3.

FIG. 7 shows the restriction enzyme analysis of the bacterial artificial chromosomes (BACs) pSM3 and pSM3FR. The BACs isolated from E. coli cultures were digested with EcoRI and the resulting DNA fragments were separated by electrophoresis on an agarose gel. The EcoRI O bands and the EcoRI Z bands are indicated and the size of the bands missing in pSM3FR is shown at the left side.

FIG. 8 shows the restriction enzyme analysis of the viral MW97.01 and wild-type MCMV genomes. The BAC vector pSM3FR was introduced into permissive embryonic fibroblasts (MEF). After several passages the viral DNA was isolated from the infected cells of the strain MW97.01 and digested with EcoRI. The resulting DNA fragments were separated by electrophoresis on agarose gels. The wild-type MCMV genome digested with EcoRI serves comparative purposes.

Figure 11:
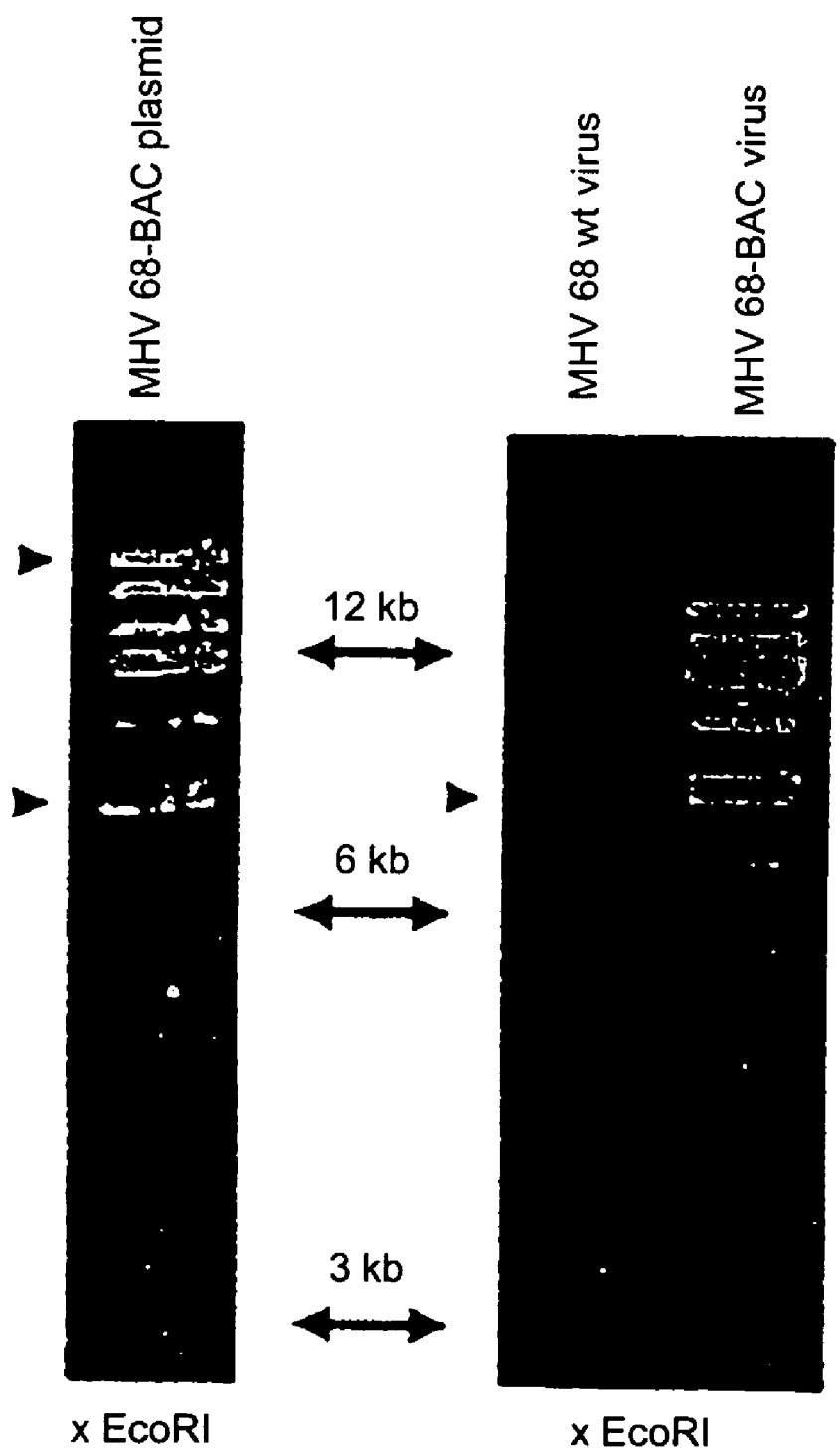

FIG. 11 shows the restriction enzyme analysis of the MHV 68 BAC vector and of the reconstituted MHV 68 genome. The BAC vector and the viral genome isolated from infected cells were digested with EcoRI and separated on an agarose gel. The wild-type MHV 68 genome digested with EcoRI serves comparative purposes.

Figure 12:
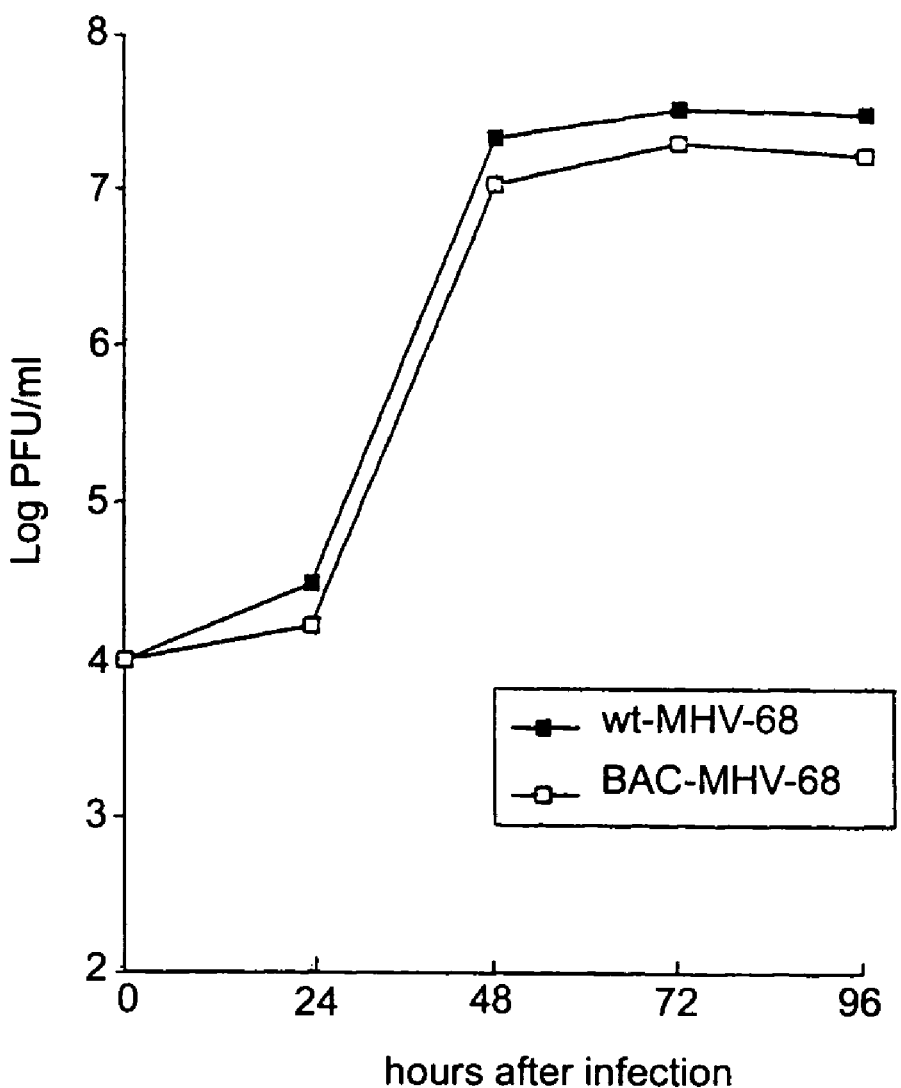

FIG. 12 shows a comparison of the growth kinetics of the MHV wild-type virus and the MHV 68 BAC virus. BHK-21 cells were infected at a moi of 0.01 and the rise of the virus titer was determined during the following 4 days.

Figure 13:
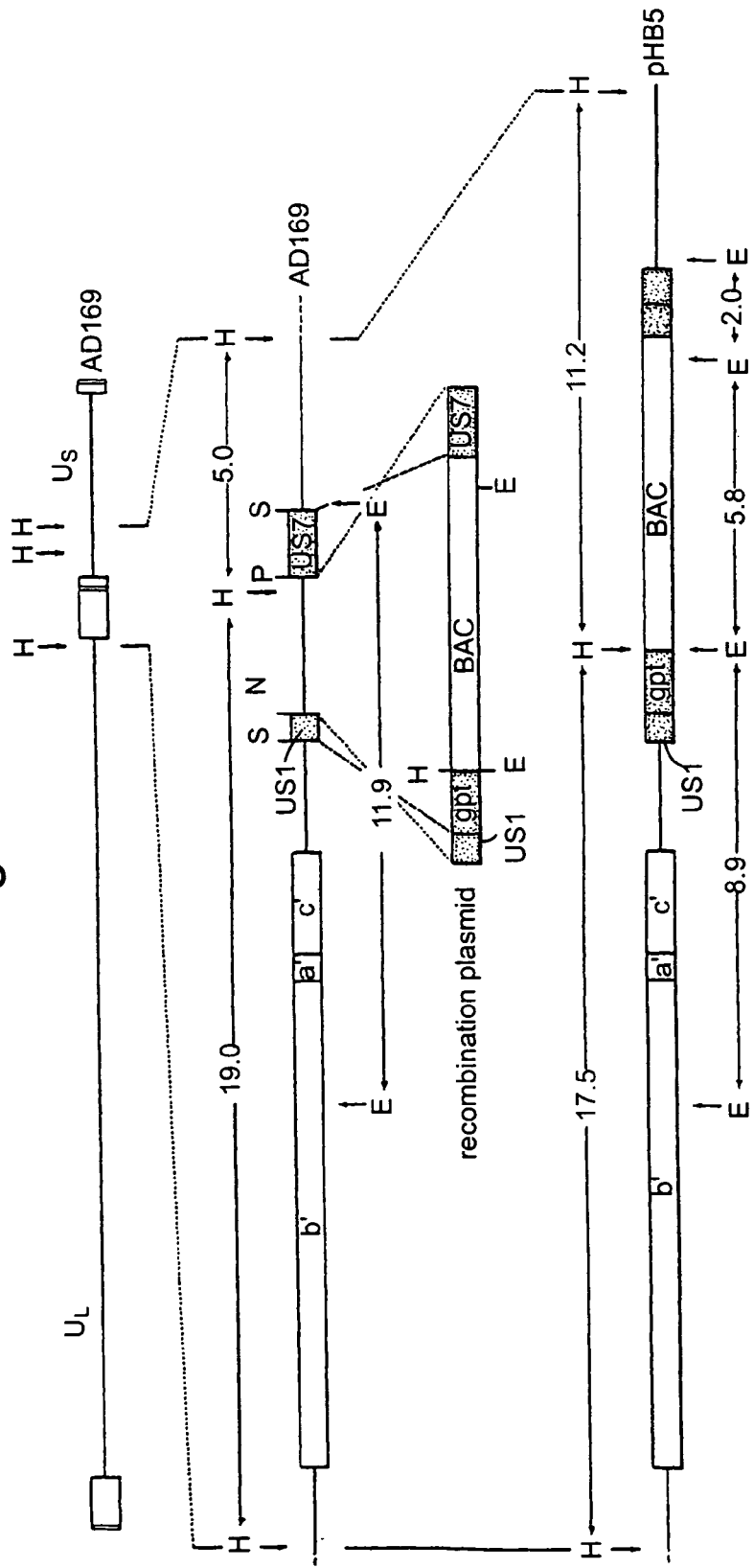

FIG. 13 shows the cloning of the genome of the HCMV laboratory strain AD169 as infectious bacterial artificial chromosome (BAC).

Figure 14:
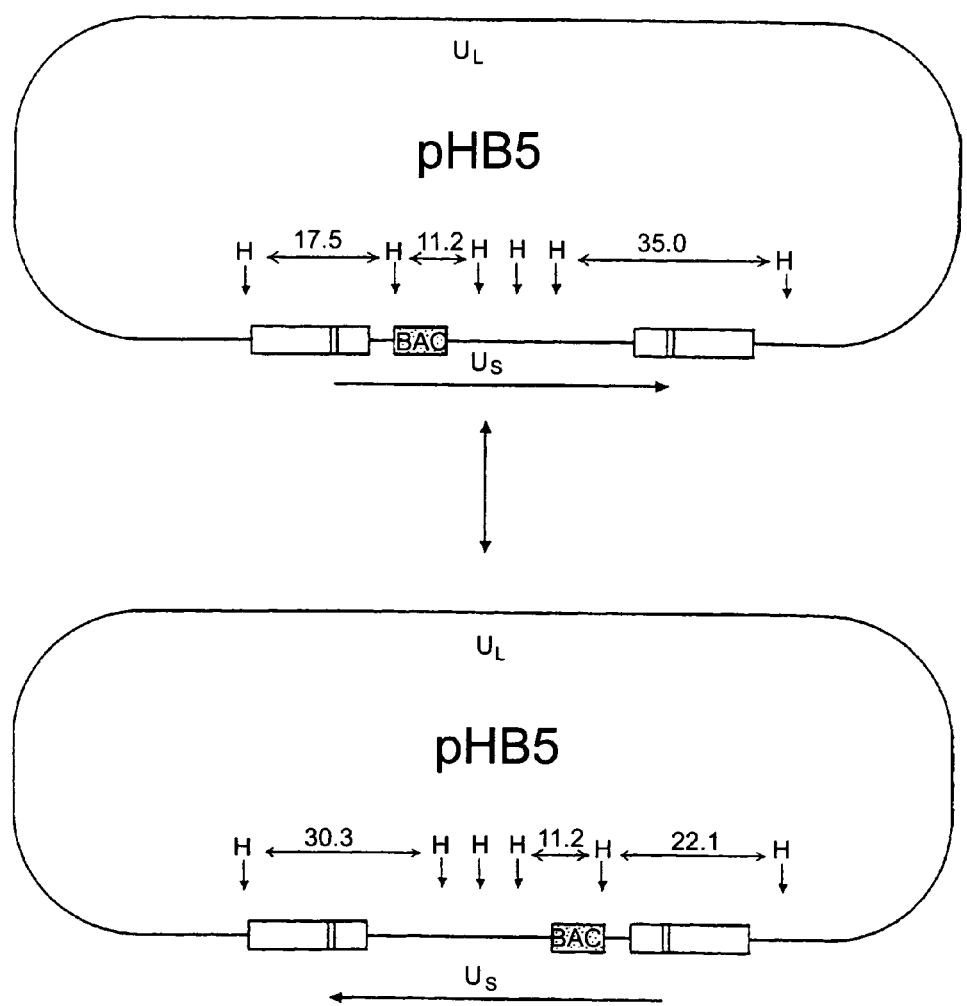

FIG. 14 shows two different isomeric forms of the HCMV BAC genome, pHB5 and pHB8.

Figure 15:

FIG. 15 shows the restriction enzyme analysis of the BAC vectors pHB5 and pHB8. Both vectors were digested with HindIII and separated on an agarose gel.

Figure 16:

FIG. 16 shows the restriction enzyme analysis of the wild-type HCMV and pHB5 genome. The viral DNA was isolated from infected cells and digested with EcoRI. Subsequently, the resulting DNA fragments were separated on an agarose gel. The arrow shows the additional 2 kb EcoRI band in the genome of pHB5.

Figure 17:
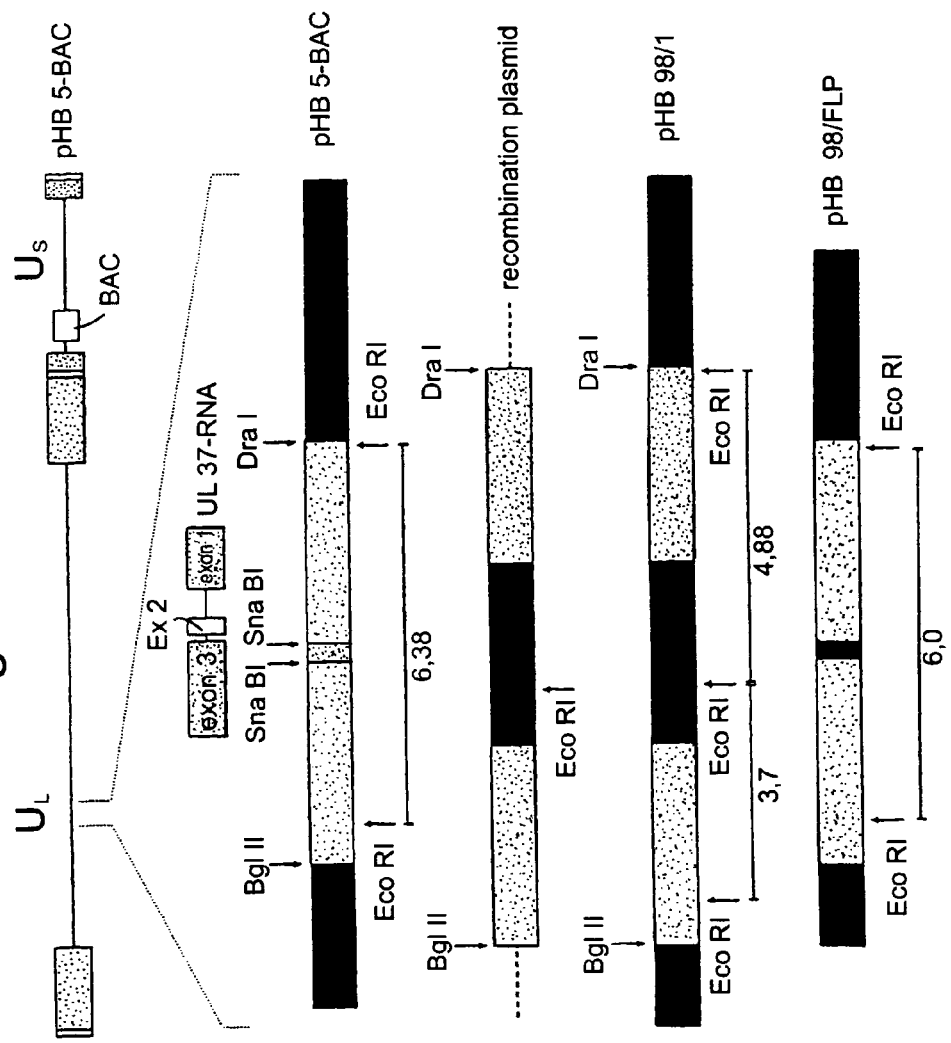

FIG. 17, shows the strategy described in Example 6 for the mutagenesis of the HCMV BAC vector pHB5.

Figure 18:
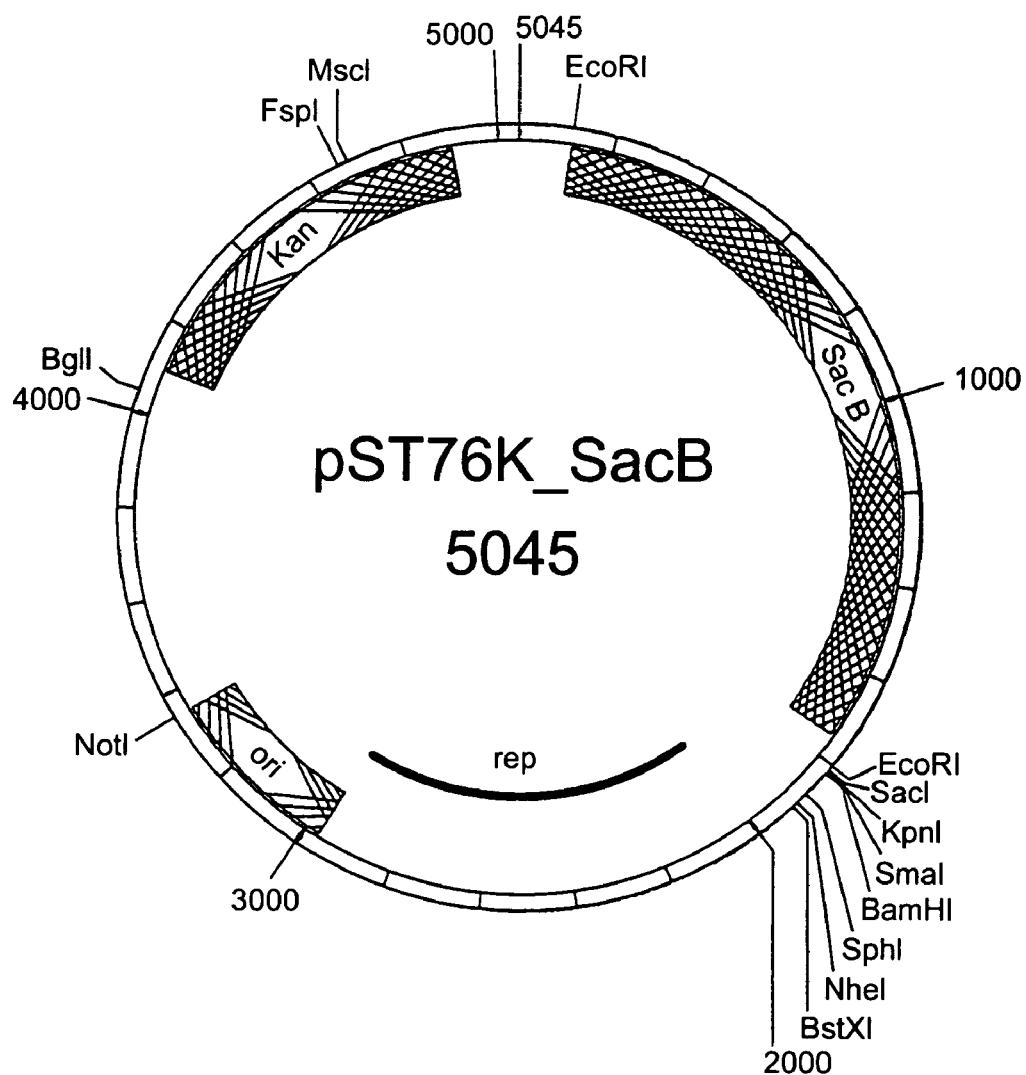

FIG. 18 shows the shuttle vector pST76K_SacB, a derivative of the pST76K vector.

Figure 19:
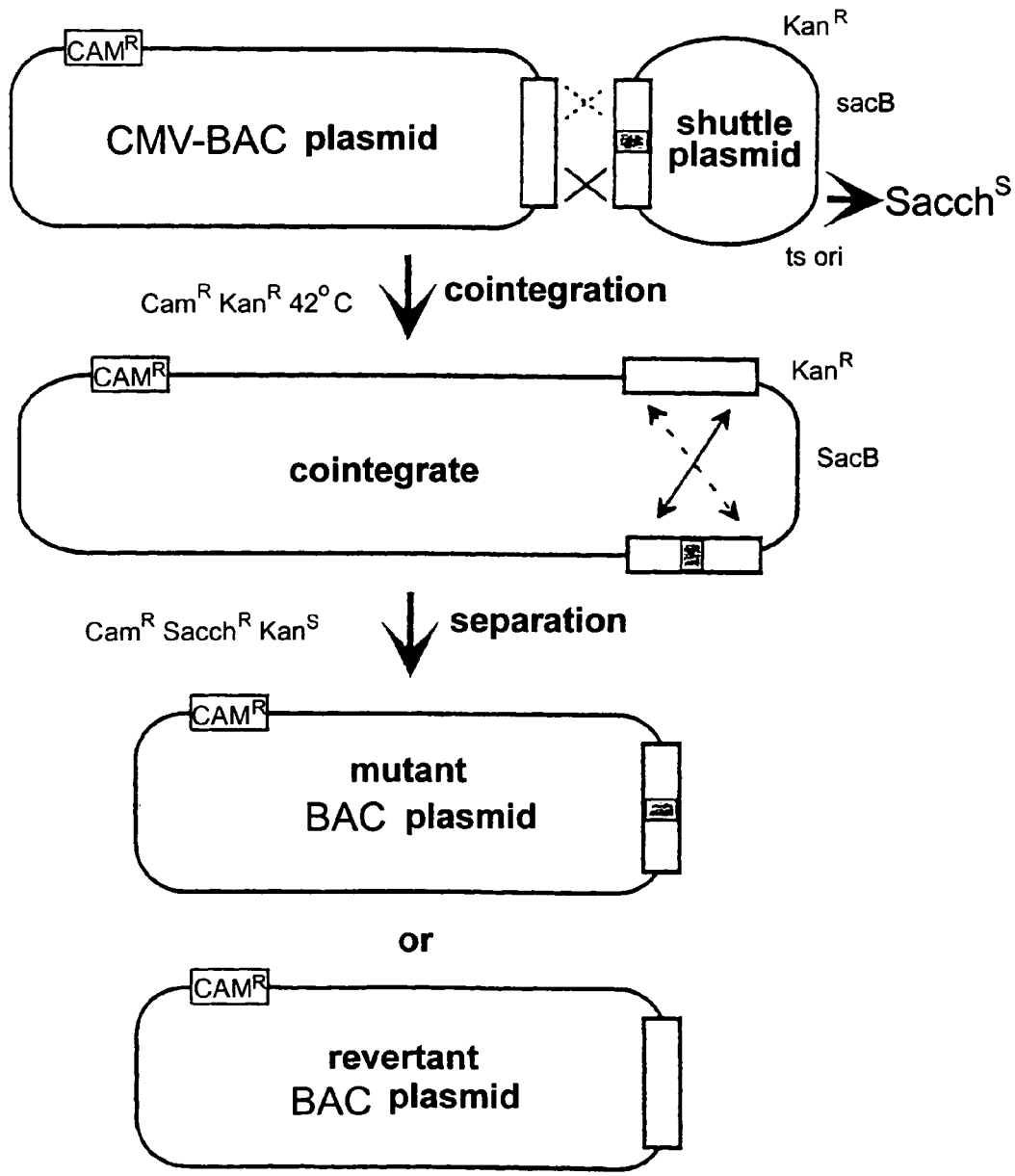

FIG. 19 shows a strategy for the mutagenesis of the CMV BAC vector in E. coli.

Figure 20:
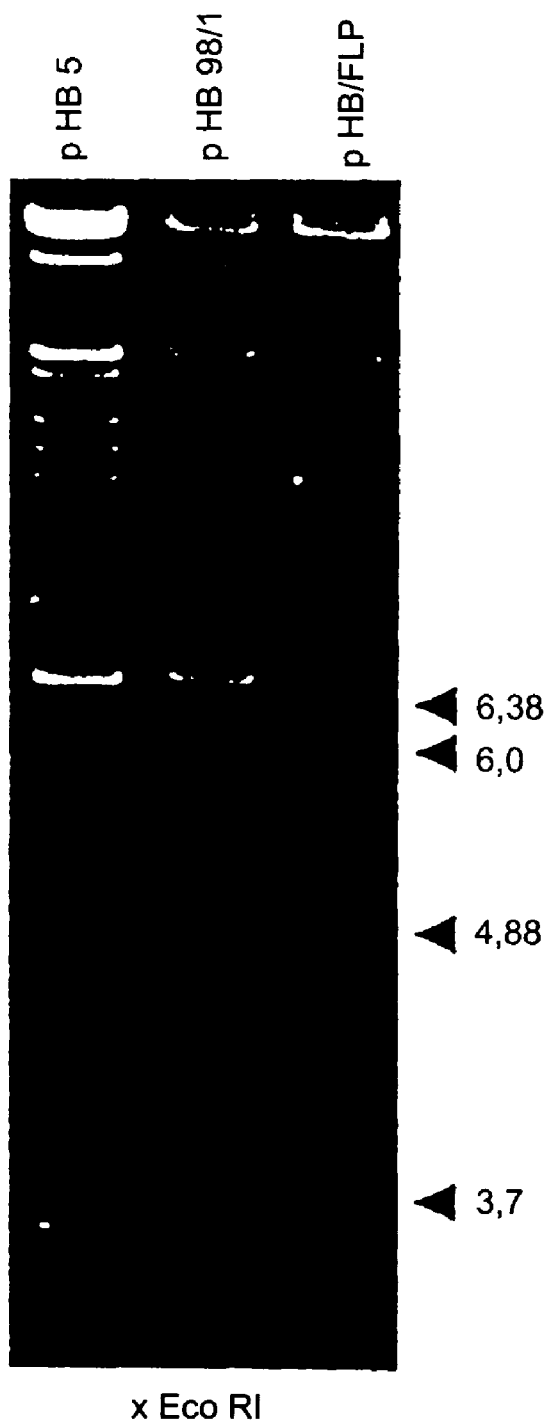

FIG. 20 shows the restriction enzyme analysis of the recombinant vectors pHB5, pHB 98/1 and pHB/FLP. The isolated DNA was digested with EcoRI and separated on an agarose gel.

FIG. 21 shows the strategy described in Example 7 for the direct transposon mutagenesis of the infectious MCMV BAC vector. (a) shows the pST76A-TnMax8 vector which is created by ligation of the pST76-A vector linearized with PstI, with the pTnMax8. (b) schematically shows the induction of the transposition into the pST76A-TnMax8 vector.

Figure 22:
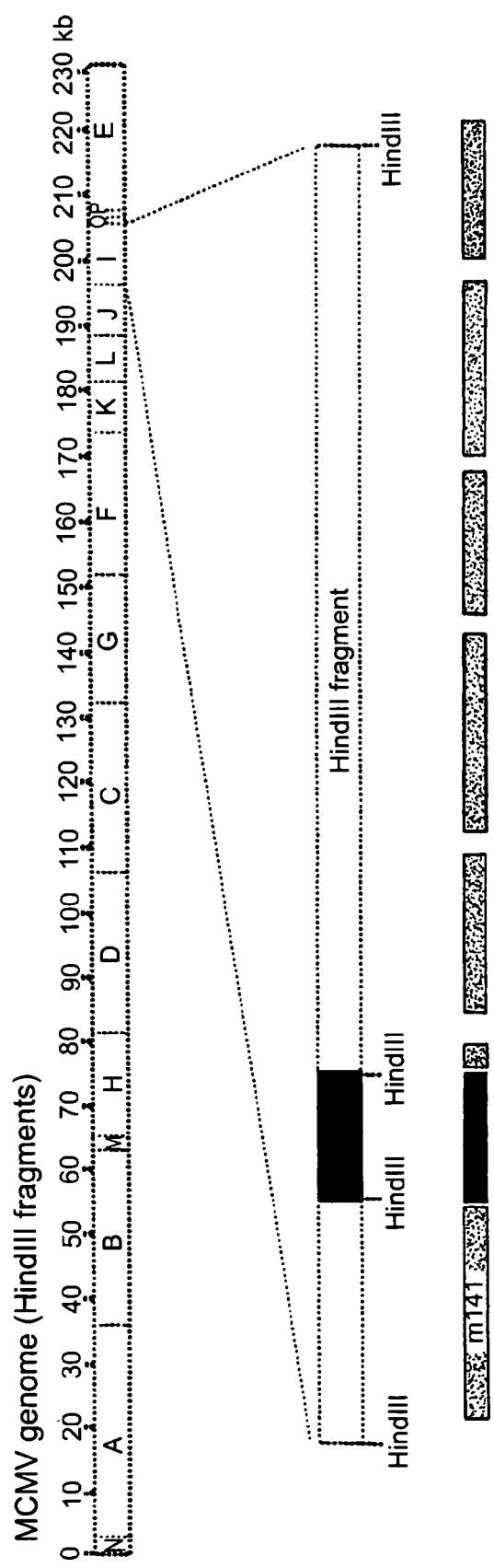

FIG. 22 shows the restriction site of the transposon in the MCMV-Kn5 clone.

Figure 23:
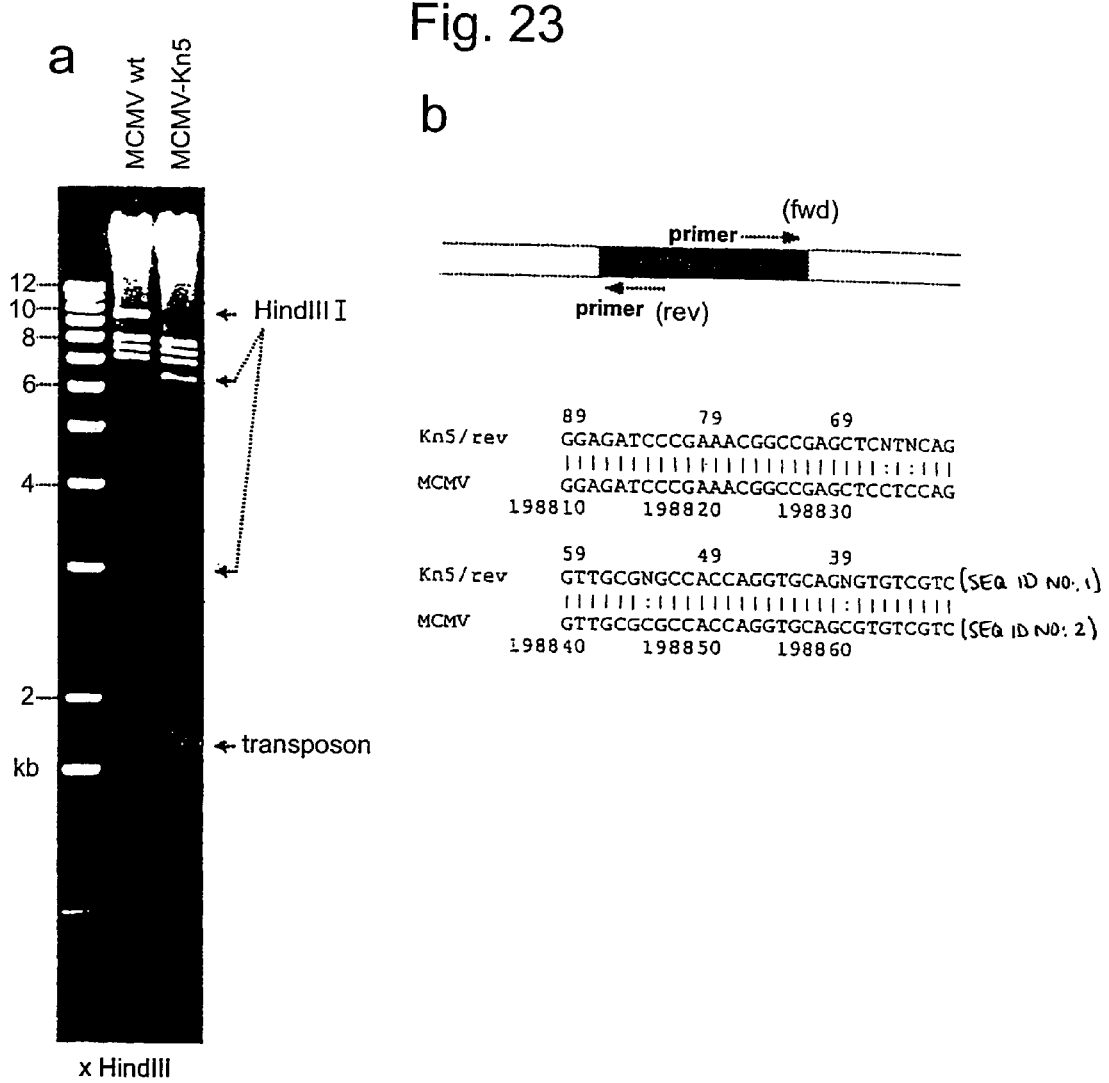

FIG. 23 shows in (a) a restriction enzyme analysis of the wild-type MCMV and MCMV-Kn5 genomes. The DNA isolated from the infected cells was digested with HindIII and separated in agarose gel. FIG. 23 (b) shows the sequencing of the clone MCMV-Kn5 with primers which bind to the ends of the transposon. The sequence obtained (SEQ ID NO: 1.1 is compared with the MCMV sequence (SEQ ID NO: 2).

Figure 24:
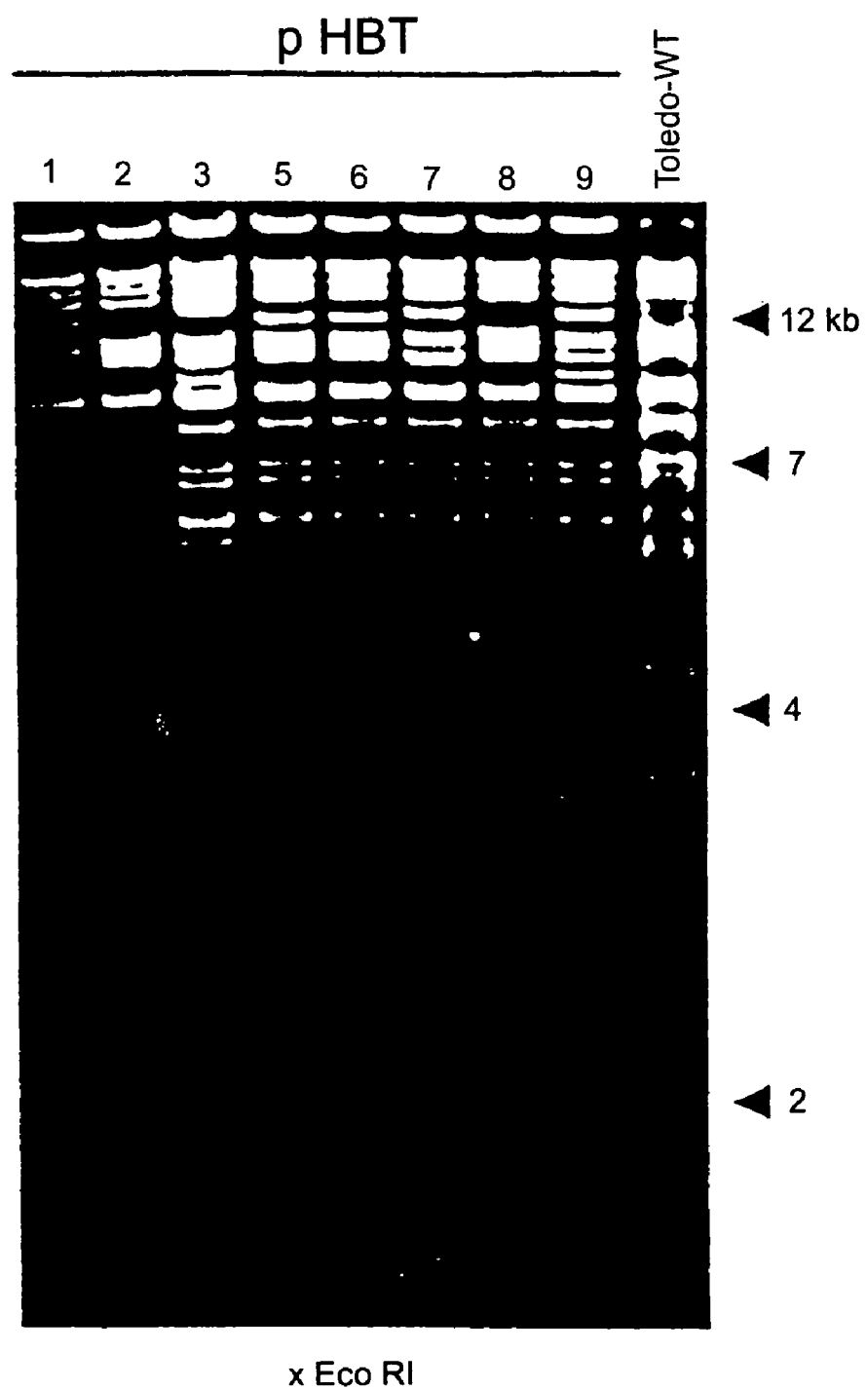

FIG. 24 shows a restriction enzyme analysis of various Toledo BAC clones. The Toledo BAC vectors were digested with EcoRI and separated on an agarose gel. The Toledo wild-type genome digested with EcoRI serves comparative purposes.

Figure 25:
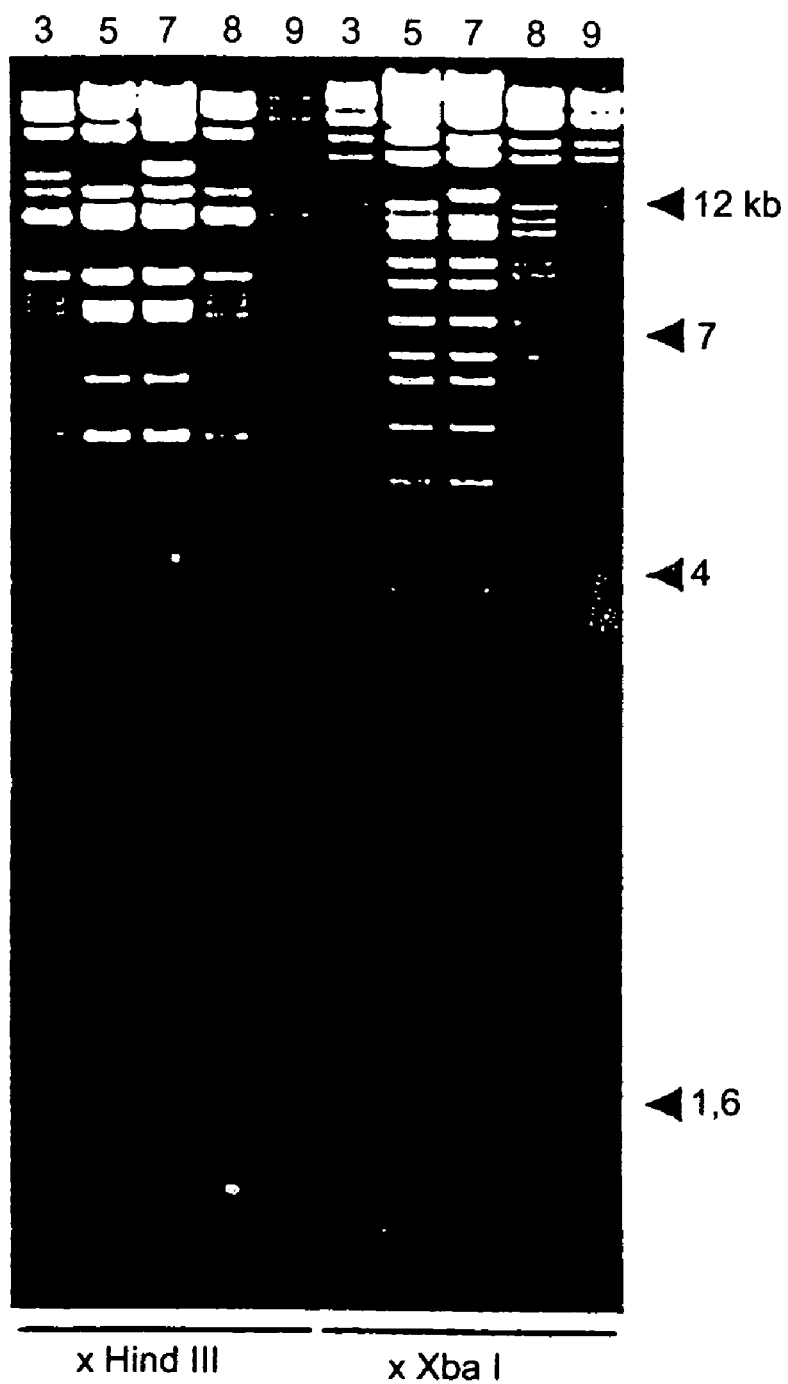

FIG. 25 shows a restriction enzyme analysis of various Toledo BAC clones with two different restriction enzymes. The first five lanes at the left side show the HindIII cleavage pattern of Toledo BAC vectors isolated from the various clones; the last five lines (right) the XbaI cleavage pattern.

The invention shall now be described in detail with reference to the examples and the figures.

EXAMPLE 1

Cloning of MCMV Genome Sequences as Infectious Bacterial Artificial Chromosome (BAC) in E. coli Generation of Viruses and Cells The propagation of MCMV (strain Smith, ATCC VR-194, ATCC, Rockville, Md.) in BALB/c mouse embryonic fibroblasts (MEF) and NIH3T3 fibroblasts (ATCC CRL1658) has been described earlier (14, 15). Recombinant viruses were generated according to published protocols (8, 9, 15). To generate virus progeny from bacterial artificial chromosomes (BACs), BACs (about 0.5-1 µg) were transfected into MEF by employing the calcium phosphate precipitation technique as described in (15, 16).

Isolation of Viral DNA and BACs

Plasmid cloning was carried out according to standard techniques (20). Restriction enzymes were purchased from New England Biolabs (Bevety, Mass.). Wild-type MCMV DNA was generated from virions, and total cell DNA was isolated from infected cells, as described earlier (14, 17). Circular viral DNA was isolated by the method of Hirt (18) and electroporated into electrocompetent E. coli DH10B strains (19). BACs were isolated from E. coli cultures using an alkaline lysis procedure (20) and purified by precipitation with polyethylene glycol (20).

Plasmids and Mutagenesis

Figure 2:
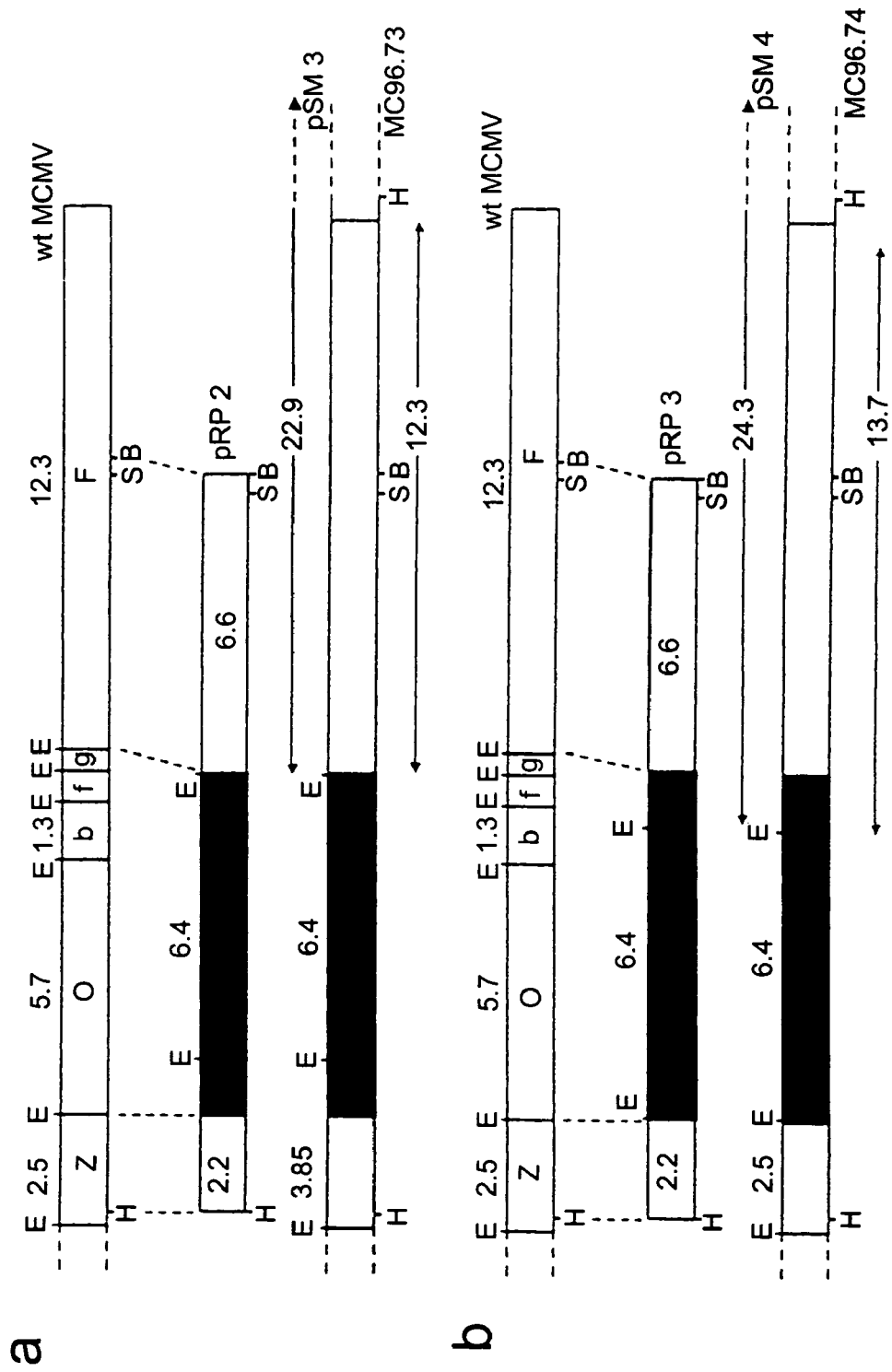

For construction of recombination plasmids pRP2 and pRP3, a 17 kb HindIII/BamHI subfragment of the MCMV HindIII E' fragment (17) was subcloned into pACYC177 (21). The EcoRI fragments 0, b, f, and g within the HindIII E' fragment (14, see FIG. 2) were deleted and an EcoRI/NotI adapter was inserted to create the plasmid pHE'ΔE. The E. coli guanine phosphoribosyl transferase (gpt) gene controlled by the thymidine kinase promoter of the herpes-simplex virus and followed by the early polyadenylation site of the SV40 early gene was flanked at one side by a tandem loxP site and then cloned, including the tandem loxP site, as NsiI/BamHI fragment into the plasmid pKSO, a derivative of the BAC vector pBAC108L (19) with a modified polylinker (PmeI-NsiI-PacI-BamHI-PmeI-AscI). To allow a mobilization of the MCMV BAC plasmid via the pBR322 mob element at a later time, a 540 by HaeIII fragment from pBR322 (nucleotides 1928-2488) was then inserted between the loxP sites of the resulting plasmid pKSO-gpt. Finally, the resulting plasmid IIBAC was linearized with NotI next to one of the two loxP sites and inserted into the unique NotI site of plasmid pHE'ΔE. pRP2 and pRP3 differ from each other in the orientation of the IIBAC sequence (FIG. 2).

To construct the mutagenesis plasmid pMieFS, a 7.2 kb HpaI/EcoRI fragment (FIG. 4a) from plasmid pIE111 (23) was inserted into plasmid pMBO96 (24), and the HindIII site in the insert was filled and destroyed by treatment with Klenow polymerase. Mutagenesis of the MCMV BAC was performed by homologous recombination in the E. coli strain CBTS (25) following published protocols (24, 25).

Construction of Recombinant MCMV

Recombinant viruses were generated either by cotransfection of viral DNA and linearized recombination plasmid, as described above (8, 15), or by electroporation of the recombination plasmid into NIH3T3 cells using the BioRad gene pulser (250 V, 960 µF), followed by a superinfection with MCMV 8 hours later. Recombinant viruses were selected with mycophenolic acid and xanthine in accordance with published protocols (9).

Isolation of Viral DNA

Wild-type MCMV DNA was prepared from virions and purified by CsCl gradient centrifugation as described previously (14). For a characterization of the reconstituted genomes, the whole cell DNA was isolated from infected cells. The cells were harvested by trypsination, followed by centrifugation at 800 g for 5 minutes, and lysed in 50 mM Tris-HCl, pH 8, 20 mM EDTA, 0.5% SDS with 0.5 mg/ml proteinase K. After incubation at 56° C. for 12 h the DNA was extracted twice with phenol/chloroform/isoamyl alcohol (50:48:2) and precipitated with ethanol. The DNA fragments were separated by electrophoresis on a 0.6% agarose gel, as described previously (14).

Circular viral DNA was isolated by the method of Hirt (18). Infected cells from a 60-mm tissue culture dish were lysed in 1 ml of buffer A (0.6% SDS, 10 mM EDTA pH 7.5), and 0.66 ml of 5 M NaCl were added, followed by incubation at 4° C. for 24 h. The samples were centrifuged at 15,000 g and 4° C. for 30 min, the supernatant was extracted with phenol, and DNA was precipitated with ethanol. The DNA was again dissolved in 30 µl TE (10 mM Tris-HCl pH 8, 1 mM EDTA) and dialyzed against TE. 10 µl of the DNA were introduced by electroporation into electrocompetent E. coli DH10B using a BioRad gene pulser (2.5 kV, 25 μF, 400 ohm). Transformants were selected on agar plates containing 12.5 μg/ml chloramphenicol.

Isolation of BACs and Reconstitution of Recombinant Viruses

BACs were isolated from 1.00 ml cultures which had been grown overnight at 37° C. in the presence of 12.5 μg/ml of chloramphenicol, using the alkaline lysing technique (20). The plasmid DNA was further purified by precipitation with polyethylene glycol (20). One tenth of the isolated plasmids (about 0.5 to 1 μg) was used for analysis by restriction enzyme cleavage or for reconstitution of the virus progeny by calcium phosphate transfection in MEF.

Metabolic Marking and Immunoprecipitation

A selective expression of wt or mutated MCMV immediate-early proteins was achieved by infection of MEF in the presence of cycloheximide (50 μg/ml) which 3 hours later was replaced by actinomycin D (5 μg/ml). Cells were then marked with [$^{35}$S]-methionine (1200 Ci/mmol; Amersham, Braunschweig, Germany) for another 3 hours. The cells were lysed and immunoprecipitations were performed using the antipeptide serum b5/1 (28, 16) and the antiserum 3/1 which is directed against the C-terminus of the IE1 protein pp 89.

Strategy for Cloning and Mutagenesis of the MCMV Genome

Figure 1:
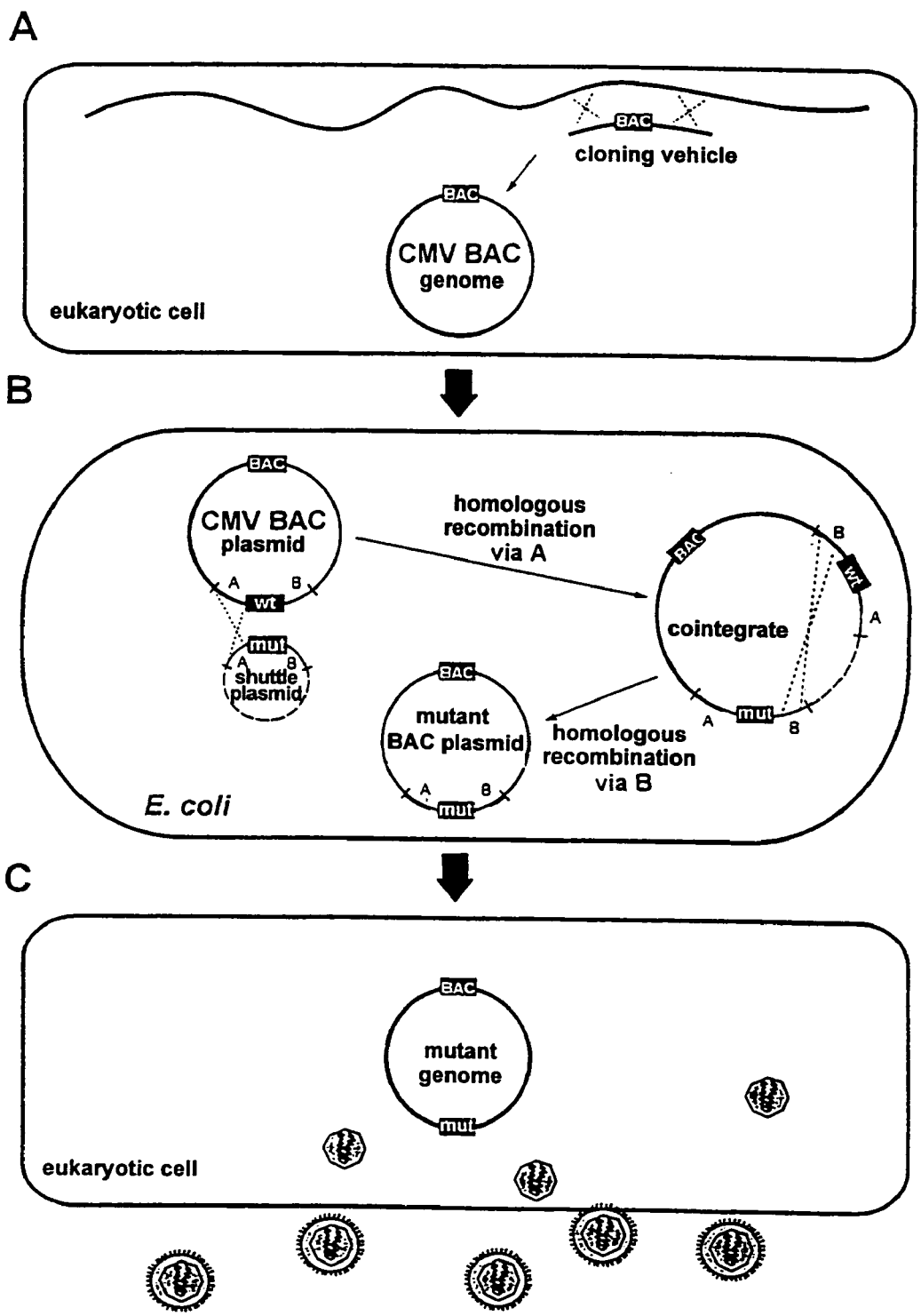

The known methods for manipulating CMV genomes and other large viral genomes are only applicable and successful to a limited degree because they are based on homologous recombination in eukaryotic cells. To make the MCMV genome and other large virus genomes more accessible to mutagenesis, infectious bacterial artificial chromosomes (BAC) of MCMV were generated in *E. coli*. Since herpesviruses circularize their genome after cell entry (6, 26), and the plasmid-like circular intermediates occur early in the herpesviral replication cycle (27), the strategy depicted in FIG. 1*a* was adopted for cloning the MCMV genome. In a first step a recombinant virus was produced that contained a bacterial vector integrated into its genome. After selection of recombinant viruses using the selection marker guanine phosphoribosyl transferase (gpt) (9) (other selection markers, such as the neomycin, hygromycin or puromycin resistance genes, are also suited therefor), circular intermediates accumulate in infected cells. After isolation and electroporation of the circular intermediates into *E. coli*, the CMV BAC is available to all genetic techniques established for *E. coli*. Transfection of the mutated BACs into eukaryotic cells should finally reconstitute viral mutants (FIG. 1).

Generation of Recombinant Viruses and BACs

We have shown previously that a large region at the right-terminal end of the MCMV genome is not essential for replication in vitro (18). Therefore, this region was chosen for integration of the BAC vector and the selection marker gpt (FIG. 2). To find out whether integration of the BAC vector into the viral genome could be achieved in both orientations, two different recombination plasmids pRP2 and pRP3 were produced (FIG. 2). For generation of BAC-containing viral genomes the recombinant virus ΔMC95.21 was used that has a lacZ insertion in the EcoRI O fragment of its genome. This allowed the identification of integration events by screening for white plaques after staining with 5-bromo-3-chloro-indolyl-β-galactopyranoside (X-Gal). Recombinant viruses with integrated vector sequences were enriched using the gpt marker. Finally, circular viral DNA was isolated from infected cells and electroporated into *E. coli*.

Figure 3:
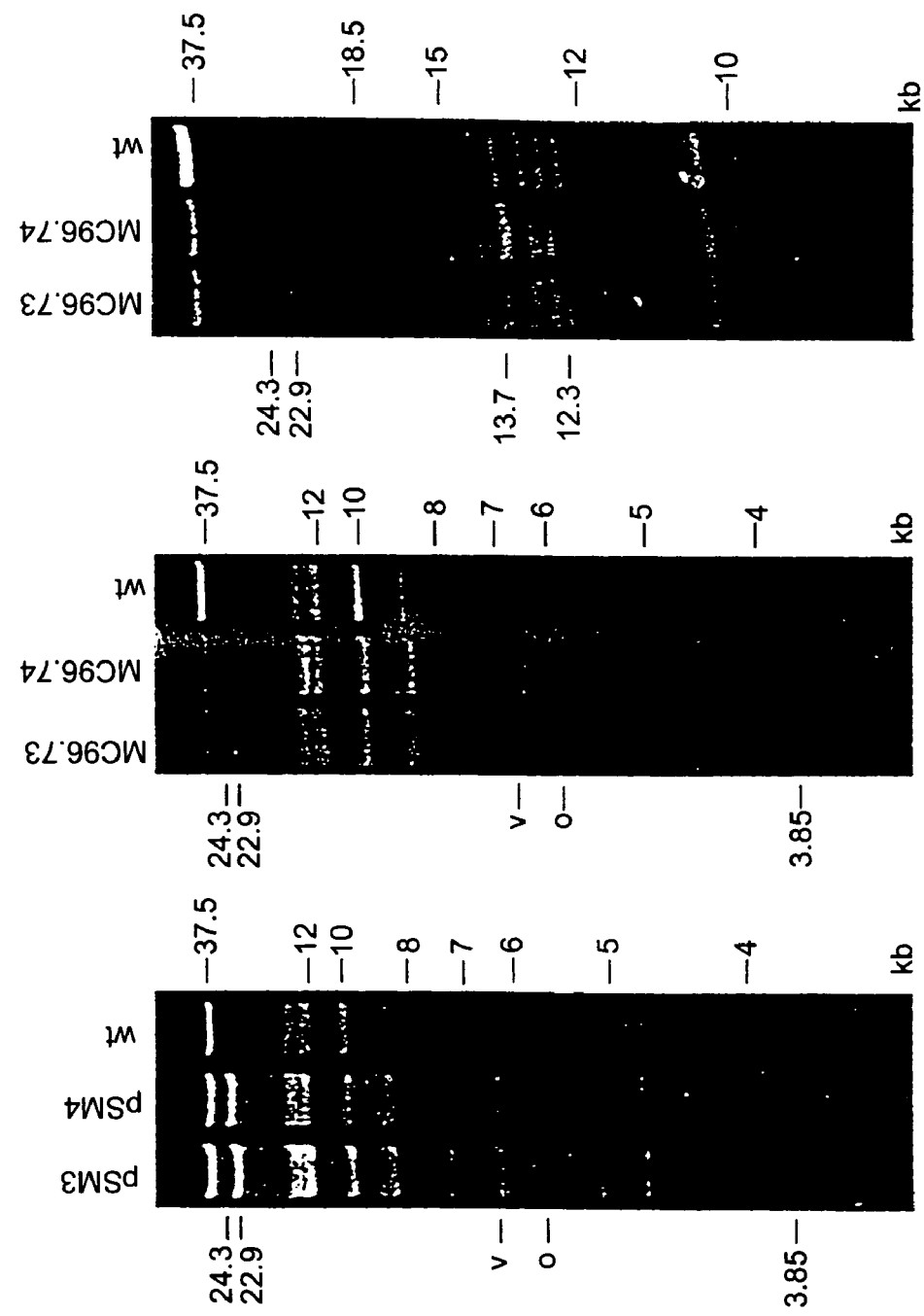

A high percentage of bacterial clones (about 80%) contained the expected complete plasmids. In comparison with DNA isolated from MCMV virions, the BACs pSM3 and pSM4 contained additional EcoRI fragments having a length of 22.9 and 24.3 kb, respectively (FIG. 3 *a*), depending on the orientation of the integrated vector (FIG. 2). The additional bands resulted from the fusion of the terminal EcoRI fragment, indicating the circular nature of the BACs (FIG. 2); as expected, the 5.7 kb EcoRI O fragment was missing in the BACs (see FIGS. 2 and 3*a*), and the vector sequences resulted in a double band at 6.4 kb (designated as v in FIG. 3*a*). In the BAC pSM3 the 2.5 kb EcoRI Z fragment was enlarged by 1.4 kb of the gpt and vector sequences, leading to a 3.85 kb fragment (FIG. 3, lane pSM3). Southern blot analysis and characterization of the BACs with restriction enzymes HindIII, XbaI and BamHI (data not shown) confirmed the successful cloning of the total genome of these MCMV recombinants into *E. coli*.

Reconstitution of Virus Progeny from MCMV BACs

Transfection of the BACs pSM3 and pSM4 into mouse embryonic fibroblasts led to the development of plaques. New cells were infected with the supernatant from cells transfected with pSM3 and pSM4. Total DNA was isolated when cells showed a complete cytopathic effect. EcoRI cleavage of the isolated DNA resulted in a similar pattern as cleavage of the BACs pSM3 and pSM4 (cf. lanes MC96.73 and MC96.74 in FIG. 3*b* and lanes pSM3 and pSM4 in FIG. 3*a*). DNA isolated from infected cells comprises circular, concatemeric and linear viral DNA, which is already packaged into capsids. Therefore, the amount of the 22.9 kb and 24.3 kb fragments resulting from the fusion of the terminal EcoRI fragments was submolar (FIG. 3*b*, lanes MC96.73 and MC96.74). Furthermore, the terminal EcoRI fragments deriving from linear genomes reappeared. The terminal EcoRI fragment (12.3 kb) was discovered in the genome of the recombinant MC96.73 and also in wild-type MCMV (FIG. 3*c*, lanes MC96.73 and wt). In the recombinant MV96.74 the terminal EcoRI fragment F was enlarged by a 1.4 kb vector sequence (see FIG. 2*b*), resulting in a double band at 13.7 kb (FIG. 2*c*, lane MC96.74). Digestion with the restriction enzymes BamHI and XbaI produced all expected bands (data not shown). Thus, it was possible to generate CMV recombinants from one large plasmid which had not been manipulated prior to transfection.

EXAMPLE 2

Construction of an MCMV IE1 Mutant by Homologous Recombination in *E. coli*

Figure 4:
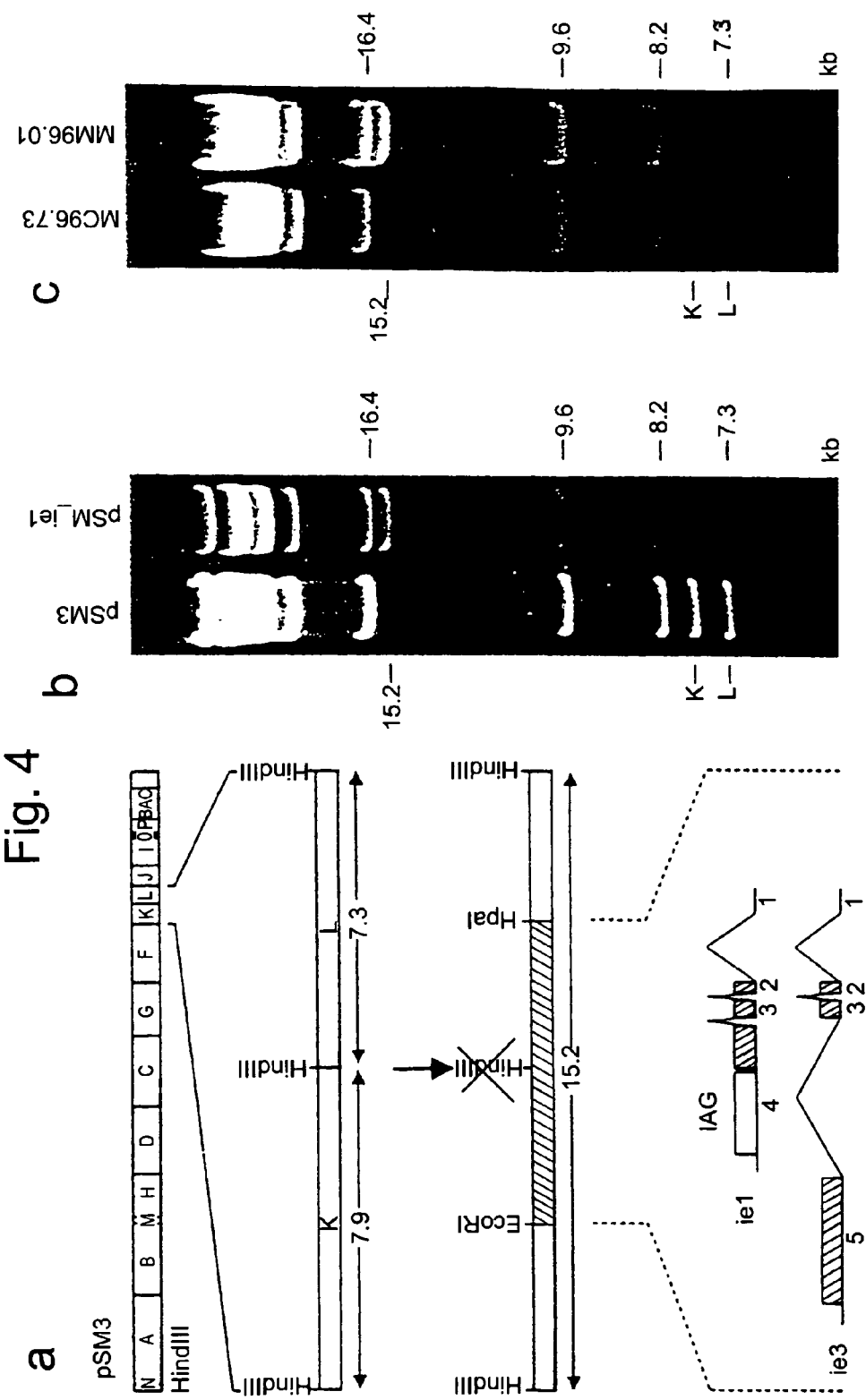

To test the efficacy of targeted mutagenesis in *E. coli*, a small mutation was introduced into the (immediate-early) (IE) region of the MCMV genome. At least two alternative spliced transcripts arise from the IE region (FIG. 4*a*) that encode the 89 kDa IE1 protein and the 88 kDA IE3 protein (16). Due to the complex structure of the IE1/IE3 transcription unit, disruption of the IE1 gene is probably difficult to achieve by conventional recombination techniques without affecting the expression of the IE3 gene. Therefore it was not known whether the MCMV IE1 protein is essential for virus replication. To disrupt the IE1 reading frame (595 codons) a reading frame mutation was introduced at a HindIII site in exon 4 of the IE1 gene. The mutation caused the original reading frame to finish after codon 273 and created a new stop codon after 9 additional codons (FIG. 4*a*). The mutation was constructed on a 7.4 kb EcoRI/PhaI fragment (FIG. 1*a*) and subsequently transferred to the BAC pSM3 by homologous recombination in E. coli employing a two-step replacement strategy (24, 25). The mutagenesis procedure resulted in the loss of the HindIII K and L fragments and the generation of a new 15.2 kb fragment (FIG. 4b). The EcoRI and BamHI patterns of the BACs were unchanged (data not shown), confirming that the BACs remained stable during the mutagenesis procedure. Transfection of the mutated BACs pSM4-IE into MEF led to plaque formation. Total DNA was isolated from infected cells and analyzed by HindIII digestion. As expected, the HindIII K and L fragments were replaced by the 15.2 kb fragment in the genome of the IE1 mutant virus MM96.01 (FIG. 4c). Obviously, the mutation introduced into the MCMV BAC was maintained after reconstitution of the mutant virus.

Figure 5:
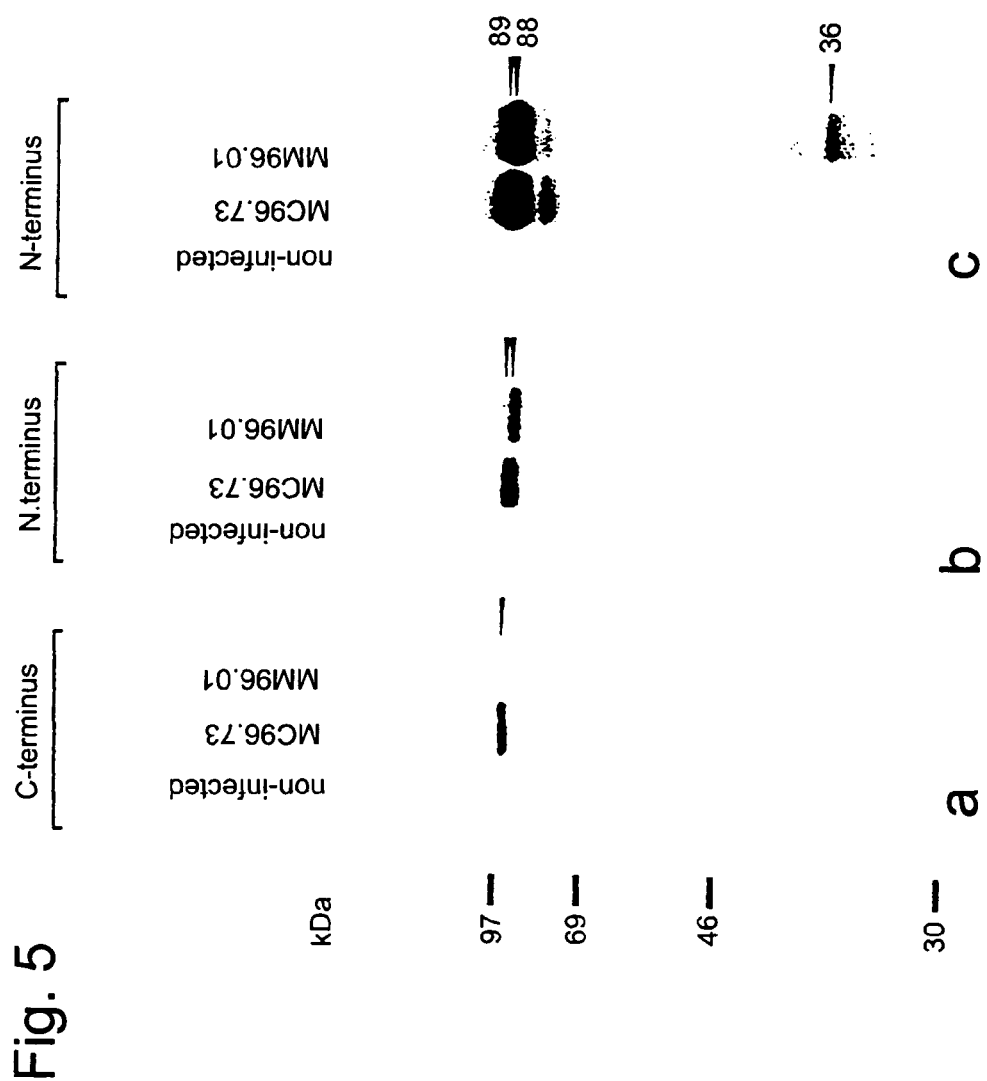

Absence of the IE1 protein in infected MM96.01 cells was confirmed by immunoprecipitation. An antiserum directed to the carboxy terminus of the IE1 protein detected the IE1 protein in lysates of MC96.73-infected cells, but did not precipitate any protein in lysates of MM96.01-infected cells (FIG. 5a). An IE1/IE3-specific antiserum, B5/1, (16, 28) detected 2 proteins of 89 and 88 kDa in lysates of MC96.73-infected cells and one protein of 88 kDa in lysates of MM96.01-infected cells (FIG. 5b). In the MM96.01 lane the 89 kDA IE1 protein was clearly missing and only the 88 kDA IE3 protein was detected (FIG. 5b). A longer exposure of the autoradiograph revealed a 36 kDA protein in MM96.01-infected cells (FIG. 5c). The apparent molecular weight of this polypeptide is in agreement with the expected molecular mass for the truncated IE1 protein and with the migration behavior of various mutated IE1 proteins (28). Thus, we draw the conclusion that the IE1 protein pp 89 is not necessary for replication of the IE mutant MM96.01.

Methods of Mutagenesis

Following the published protocols of O'Connor et al. (24) and Kempkes et al. (25), mutagenesis of the MCMV BACs was performed by homologous recombination in the E. coli strain CBTS which carries a recA allele and a temperature-sensitive suppressor (25). The BAC pSM3 and the shuttle plasmid pMieFS were successively electroporated into E. coli CBTS, and clones which contained cointegrates were selected at 42° C. on agar plates with chloramphenicol (12.5 µg/ml) and tetracyclin (10 µg/ml). The cointegrates were analyzed for the desired structures by restriction enzyme analysis. The separation of the cointegrates was made possible by incubation of the bacterial clones at 30° C. on agar plates only with chloramphenicol. The plasmids were identified by screening for tetracyclin-sensitive clones and analyzed by HindIII cleavage to determine whether a mutation had been achieved or whether there had been a return to the parental sequence.

EXAMPLE 3

Reconstitution of the Complete MCMV Genome in E. coli (Example of Insertion) and Excision of the Vector Sequences After Transfection of the BAC Plasmids in Permissive Cells Due to its construction the MCMV BAC plasmid pSM3 (see Example 1) lacks 8 kb of the MCMV genome. To be able to generate MCMV mutants based on the complete MCMV genome, a BAC plasmid was constructed that contained the complete MCMV genome. To this end the missing 8 kb were inserted into pSM3 by homologous recombination in E. coli. The resulting plasmid was named pSM3FR (cf. FIG. 6).

For the construction of the shuttle plasmid, a 10.9 kb HindIII/AvrII fragment from the HindIII E' fragment of the MCMV strain K181 (17) was cloned into the plasmid pACYC184 (21) by using an oligonucleotide adapter with the cleavage sites XbaI-NotI-BamHI-SpeI-HindIII-BamHI. Subsequently, a 2.0 kb NotI/XbaI fragment (homology B in FIG. 6) from the plasmid KSO-gpt (cf. Example 1) was inserted next to the 10.9 kb HindIII/AvrII fragment (using the cleavage sites NotI and SpeI in the region of the oligonucleotide; cf. FIG. 6, center, "shuttle-plasmid"). The complete insert was then ligated as 12.9 kb HindIII fragment into the HindIII-cut plasmid pMBO96 (24). Mutagenesis was carried out as described in Example 1.

Figure 6:
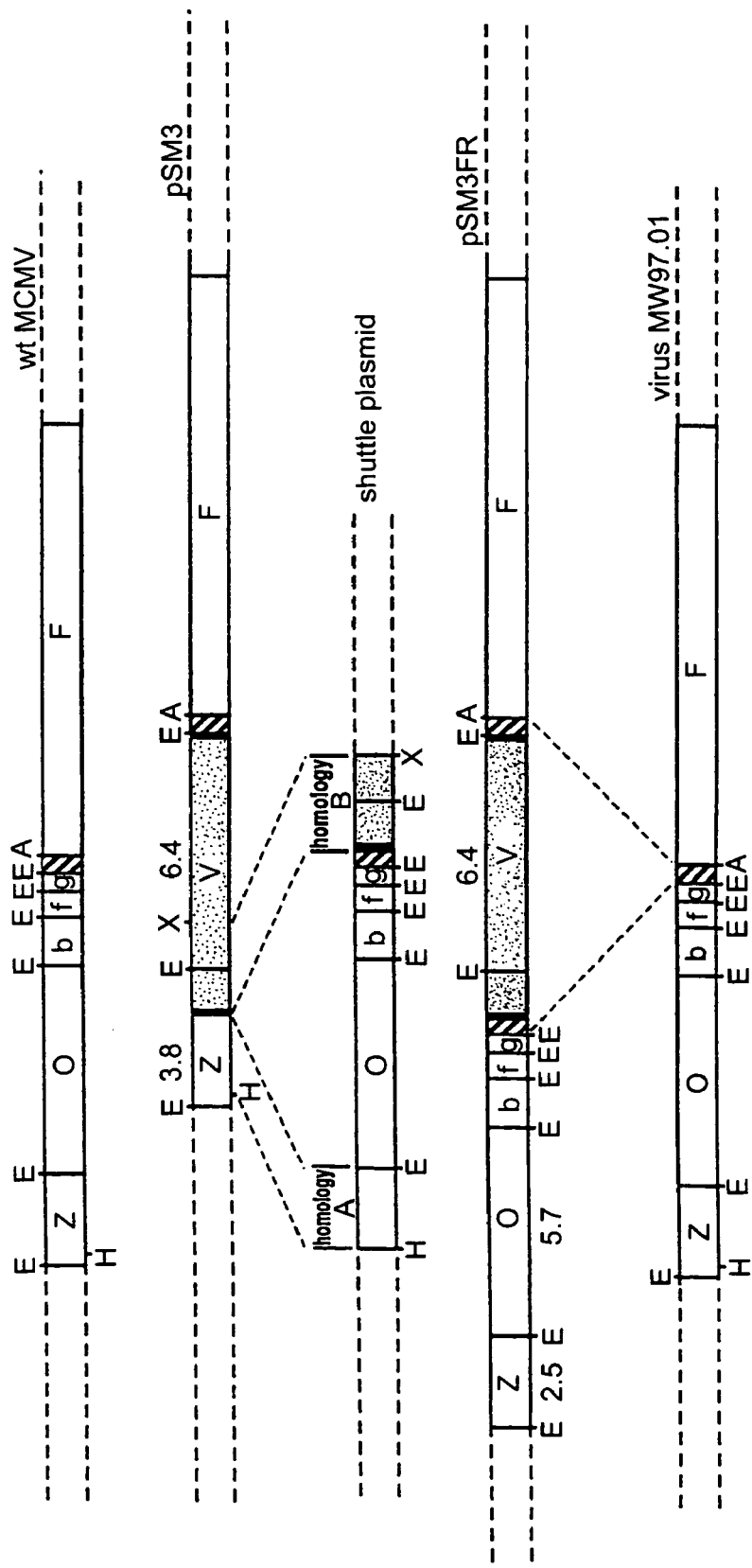
Figure 7:
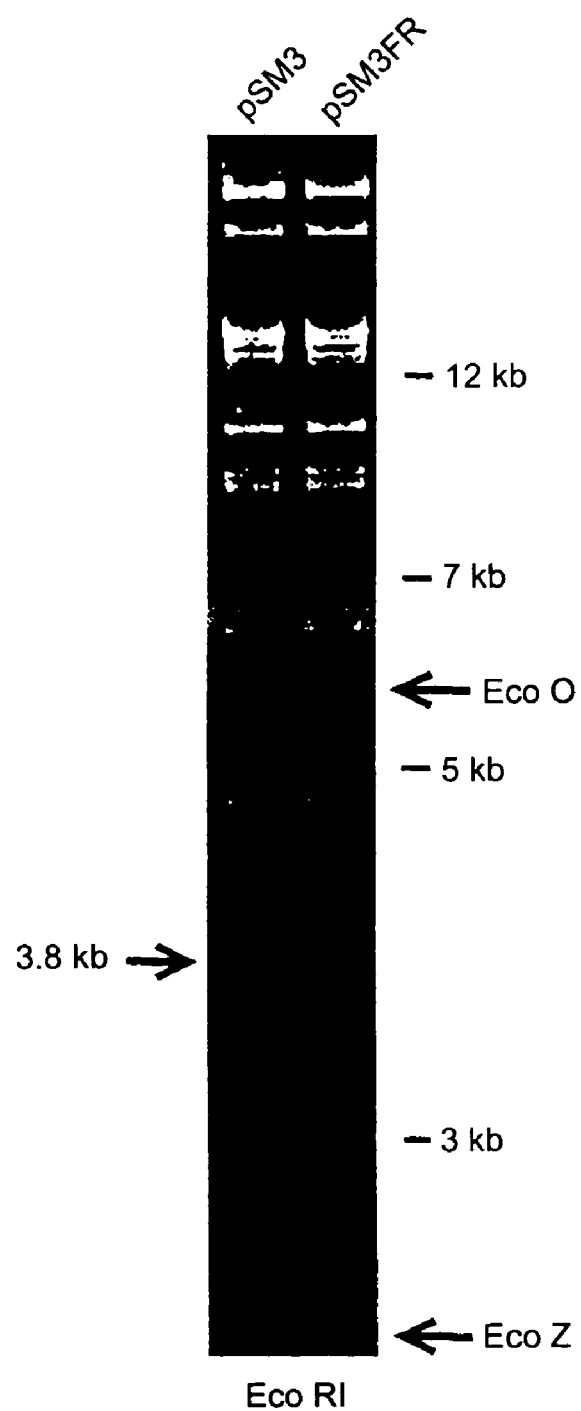

FIG. 7 shows the EcoRI cleavage pattern of the MCMV BAC plasmids pSM3 and pSM3FR. In comparison with plasmid pSM3, a 3.8 kb EcoRI band is missing in plasmid pSM3FR, as expected, and the 5.7 kb EcoRI 0 and the 2.5 kb EcoRI Z bands are present again as in the MCMV wt genome (cf. the schematic representation of the expected structure of the BAC plasmids pSM3 and pSM3FR in FIG. 6). The EcoRI fragments b, f and g are also present in pSM3FR (because of their small size they have a greater mobility in agarose gels and are not contained in the gel section shown in FIG. 7).

Hence, the BAC plasmid pSM3FR contains the whole MCMV genome and the BAC vector pKSO-gpt flanked by loxP sites (black areas in FIG. 6).

During insertion of the missing 8 kb a 527 by EcoRI/AvrII fragment was also inserted at the left side from the vector sequences, which fragment already existed at the right side from the vector sequences (hatched in FIG. 6). Thus this region is present twice in the BAC plasmid pSM3FR and flanks the BAC vector sequences (marked in grey in FIG. 6).

Identical sequences are required for homologous recombination. The BAC vector sequences were flanked with the 527 by fragment with the aim to cut out the vector sequences by homologous recombination after transfection of the BAC plasmid pSM3FR in permissive eukaryotic cells. In the E. coli strain CBTS (25) the BAC plasmid pSM3FR is stable because in said E. coli strain considerably larger homologous regions are needed for effecting a homologous recombination.

Figure 8:

After transfection of the BAC plasmid pSM3FR in permissive embryonic fibroblasts (MEF) a spontaneous excision of the vector sequences from the MCMV BAC genome by homologous recombination via the 527 by sequences was observed. After a few passages of the reconstituted virus in said cells, the vector sequences are not detectable any more (neither by Southern blotting nor by PCR). A comparison of the EcoRI cleavage pattern of the wild-type MCMV genome with that of the MW97.01 genome (which was regenerated from the BAC plasmid pSM3FR) does not reveal any differences (FIG. 8). Since the inserted 8 kb derive from the genome of the MCMV strain K181 and exhibit small sequence differences (polymorphism) with respect to the used wild-type MCMV strain Smith, we have however not been able to furnish clear proof that the MW97.01 virus genome derives from the BAC plasmid pSM3FR.

Evidently, MCMV genomes which have lost the bacterial vector sequences are much better packaged into virus particles than MCMV genomes with vector sequences because the latter have an excessively long genome.

Hence, flanking of the BAC vector with identical sequences can be used for removing the vector sequences from the virus genome again. This method seems to be especially suited when used in combination with selection pressure against an excessively long genome. The method is an alternative to the excision of the vector sequences with recombinase Cre (cf. Example 4).

Figure 9:
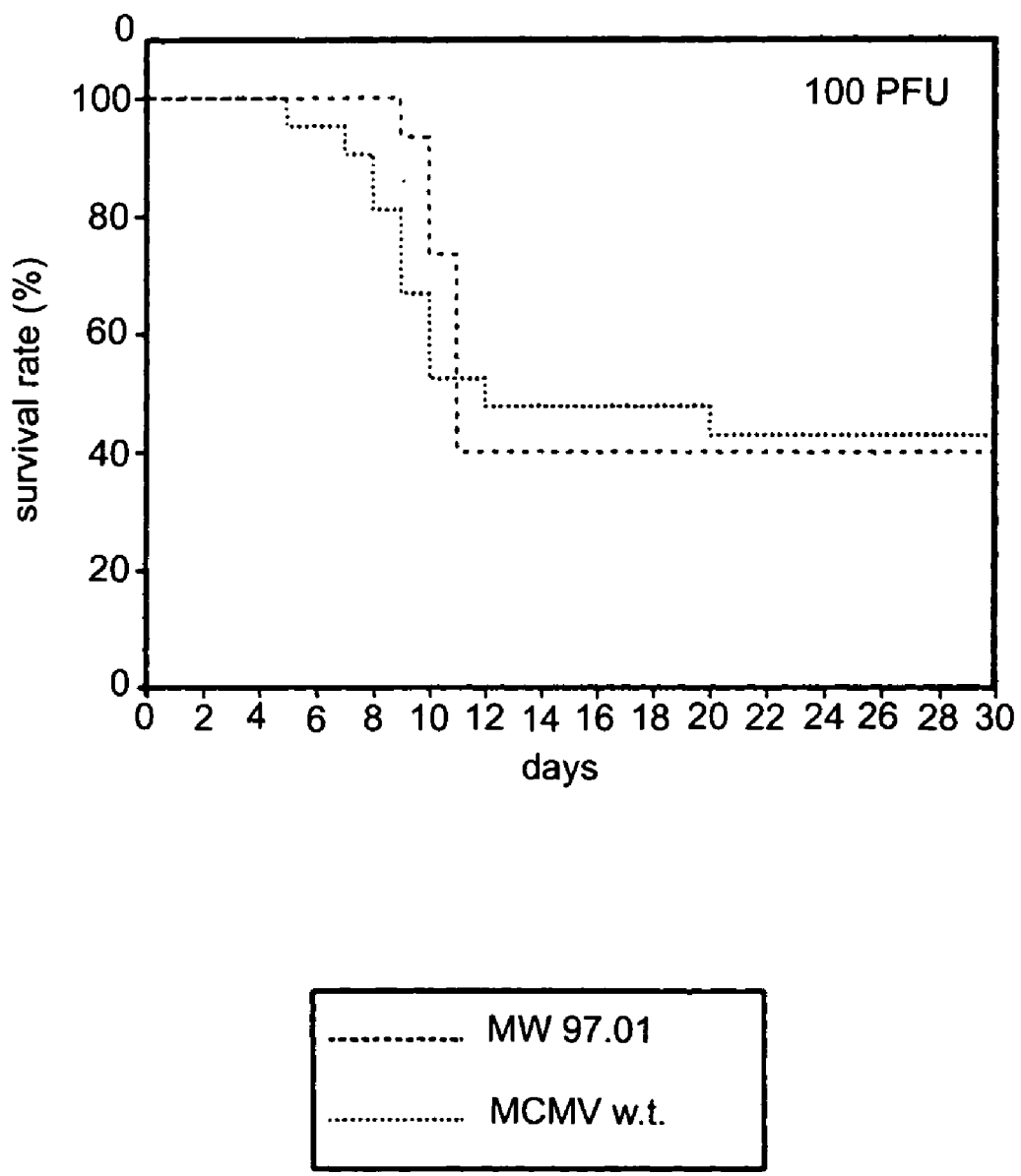
FIG. 9 shows the survival rates of newborn mice which were infected with MW97.01 and MCMV wt Smith, respectively.

The virus MV97.01 derived from the MCMV BAC plasmid pSM3FR was compared as to its virulence in newborn mice with the MCMV wild-type strain Smith. FIG. 9 shows identical survival rates of mice which were infected with MW97.01 and MCMV wt Smith, respectively. The virus titer in different organs was also comparatively high (data not shown). Hence the virus MW97.01 has the same biological characteristics as the wild-type MCMV virus. This demonstrates that the passaging of the MCMV genome in E. coli does not lead to spontaneous changes in the MCMV genome and the biological characteristics of the regenerated virus.

EXAMPLE 4

Figure 10:
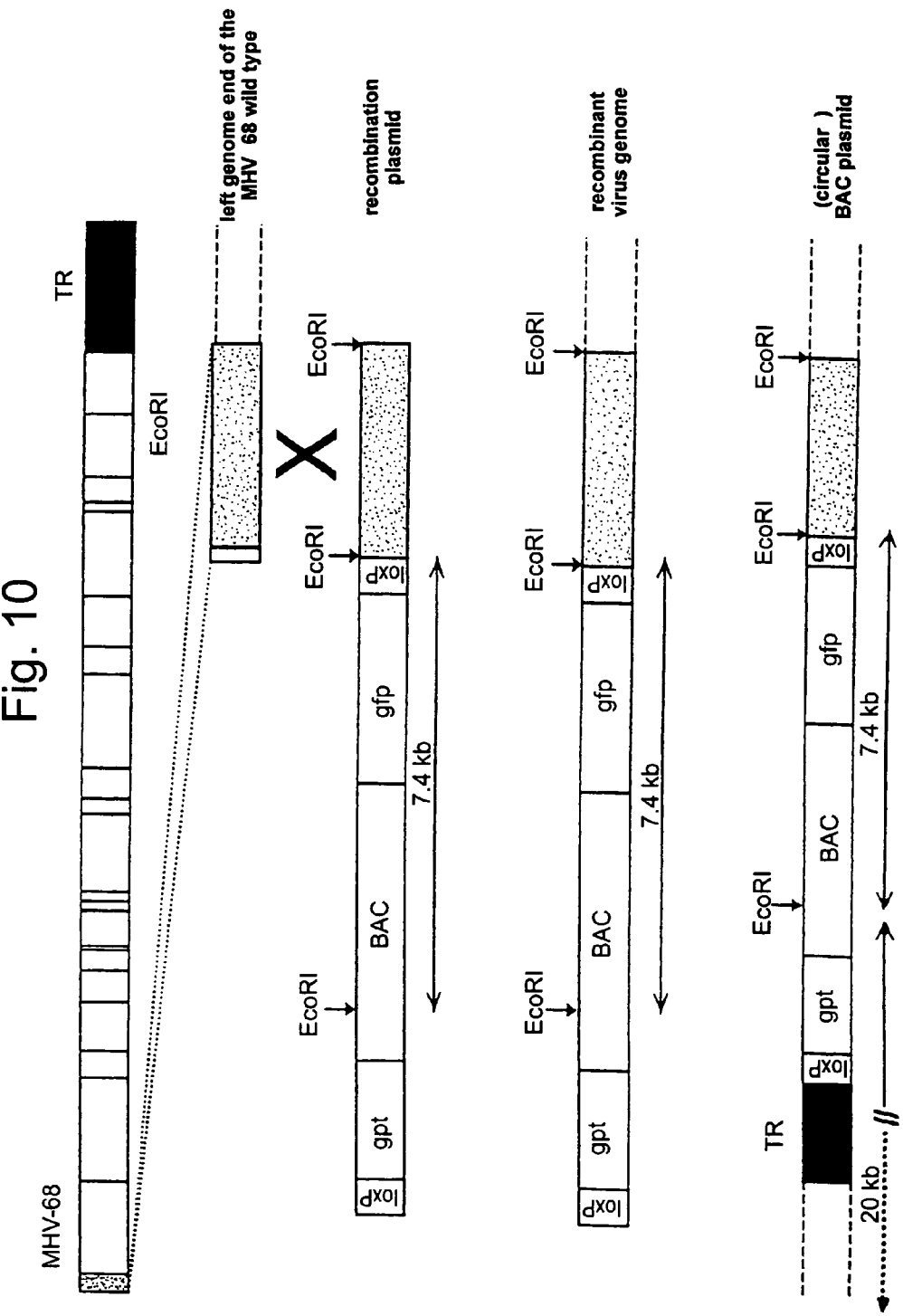
FIG. 10 shows the strategy for cloning the genome of the murine gammaherpesvirus 68 as infectious bacterial artificial chromosome (BAC) in E. coli, as described in Example 4.

Cloning of the Genome of a Gammaherpesvirus (Murine Gammaherpesvirus 68-MHV 68-) as Infectious Bacterial Artificial Chromosome (BAC) in E. coli and Reconstitution of MHV 68 Viruses This example shows the cloning of a gammaherpesvirus genome in an exemplary way. The mouse gammaherpesvirus 68 (MHV 68) is a natural pathogen for mice and is similar in its biology and genome organization to the human herpesviruses Epstein-Barr virus and HHV8 (29). Infection of mice with MHV 68 is therefore an excellently suited model system for analyzing the pathogenesis of gammaherpesvirus infections. The genome of the murine gammaherpesvirus 68 (MHV 68) contains a variable number of terminal repeats at its ends (TR; FIG. 10, top). The MHV 68 genome can compensate insertions through a reduced number of terminal repeats. Recently, it has been found that insertions at the left end of the genome of MHV 68 are possible by crossing over at one side with the linear virus genome (30). Therefore, the BAC vector sequences were inserted by unilateral crossing over at the left end of the genome.

For the construction of the recombination plasmid a 1.5 kb large EcoRI fragment from the left end of the genome was generated by PCR with MHV 68 DNA as template and cloned into the EcoRI site of the' plasmid pMHV3 (a pK18 derivative whose polylinker was previously modified by insertion of an oligonucleotide (new cleavage sites: MluI-NotI-AvrII-SgrAI-PacI-SgrAI-EcoRI-ApaLI-MluI)). (pk18 is a derivative of pUC18 which contains a kanamycin resistance gene instead of the ampicillin resistance gene). The BAC vector pKSO-gpt (cf. Example 1) was then inserted via a PacI site left from the EcoRI fragment (cf. FIG. 10; third line: "recombination plasmid"). Finally, using an MiuI/PstI adapter, a 1.6 kb large NsiI/MluI fragment of the plasmid EGFP (Clontech), containing the HCMV major immediate-early promoter, the coding sequence for the green-fluorescent protein (gfp) and the polyA signal of SV40, was cloned into an NsiI site between the BAC vector sequences and the right loxP site (cf. FIG. 10, "recombination plasmid").

5 µg of the recombination plasmid were cleaved with MluI to release the insert (loxP-gpt-BAC-vector-gfp-loxP homologous region). The insert was introduced by electroporation together with about 2 to 5 µg of viral MHV 68 DNA (isolated from MHV 68-infected BHK 21 cells) into BHK-21 cells. Recombination between the homologous sequences of the linear MHV 68 genome and of the recombination plasmid (grey in FIG. 10, 2nd and 3rd lines) should result in the insertion of the BAC vector and in the production of the recombinant viral genome (4th line in FIG. 10). Ligation of the right genome end (with the terminal repeats) to the left end of the genome (which now contains the BAC vector) leads to the production of a circular MHV 68-BAC genome which can be isolated from infected cells, electroporated into E. coli and finally propagated in E. coli as a BAC plasmid.

After electroporation of the BHK-21 cells with viral DNA and recombination plasmid plaques were formed. When a complete cytopathic effect had been achieved, the virus was transferred to new BHK21 cells and subjected to a selection with xanthine (25 µM) and mycophenolic acid (100 µM) (9, 11). This should lead to an enrichment of viruses which have the BAC plasmid with the selection marker gpt integrated into their genome. Under the fluorescence microscope green-stained cells could be detected, which is an indication of the integration and expression of the gfp gene. After three selection rounds with xanthine and mycophenolic acid, circular MHV 68 DNA was isolated from infected BHK21 cells, electroporated into E. coli DH10B and plated on agar plates with chloramphenicol (12.5 µg/ml) (cf. Example 1). Plasmid isolation with subsequent restriction digestion led to the identification of an E. coli clone which contained a BAC plasmid with a complete MHV 68 genome.

Restriction digestion of the MHV 68-BAC plasmid with EcoRI showed—in comparison with EcoRI-cleaved MHV 68 wild-type virus DNA—a double band at 7.4 kb and an additional band at about 20 kb (FIG. 11; cf. lane MHV-68 BAC plasmid with lane MHV 68 wt virus; differences are marked with black arrow tips). The additional 7.4 kb band (which leads to the formation of the double band) derives from the BAC vector portion and the additional, approximately 20 kb large band results from the circular nature of the plasmid (whereas the approximately 20 kb large band is missing in lane MHV 68 wt virus because the MHV 68 virus DNA predominantly contains linear genomes; cf. schematic representation of the MHV-68 BAC plasmid in FIG. 10, bottom). Restriction digestion of the BAC plasmid with other restriction enzymes confirmed the expected structure of the MHV 68-BAC plasmid.

Transfection of the MHV 68-BAC plasmid into BHK21 cells led to the formation of plaques. This demonstrates that the MHV 68-BAC plasmid is "infectious" and contains all essential genes, and that no undesired mutations appeared during the propagation of the plasmid in E. coli. Under the fluorescence microscope, infected cells showed a green stain, i.e., as expected, the gfp gene is contained in the genome of the reconstituted viruses. DNA of the MHV 68-BAC virus was isolated from infected cells, digested with EcoRI and separated on an agarose gel (FIG. 11, lane "MHV 68-BAC virus"). The EcoRI cleavage pattern of the MHV 68-BAC virus DNA is, as expected, substantially identical with the EcoRI cleavage pattern of the MHV 68 wt virus DNA (FIG. 11); the approximately 20 kb large EcoRI band has disappeared because the MHV 68-BAC virus DNA isolated from infected cells also predominantly comprises linear genomes.

FIG. 12 shows a comparison of the growth kinetics of MHV wild-type virus and MHV 68-BAC virus. BHK21 cells were infected at a moi of 0.01 and the rise of the virus titer was determined during the following 4 days.

The growth kinetics of the two viruses is identical, which is further evidence that the MHV 68-BAC genome codes for all viral functions and that propagation of the MHV 68-BAC genome is possible in E. coli.

The BAC vector sequences (with the gpt and the gfp gene) can be removed again with the recombinase Cre (22) via the loxP sites in the MHV 68-BAC genome (cf. FIG. 10). An MHV 68 genome can thereby be generated that, except for a loxP site, is identical with the wild-type MHVC 68 genome. The BAC vector sequences were deleted by passaging the MHV 68 BAC-virus into a cell line expressing recombinase Cre. Cells infected with the resulting viruses had no green staining, which is evidence that the BAC vector sequences, including the gfp gene, were deleted.

EXAMPLE 5

Cloning of the Genome of the HCMV Laboratory Strain AD169 as Infectious Bacterial Artificial Chromosome (BAC) and Reconstitution of Cytomegaloviruses from Transfected HCMV-BAC Plasmids For insertion of the BAC vector, the region between the genes US1 and US7 in the unique-short (US) region of the HCMV genome was selected because it was known that said region contains genes which are not essential for replication of HCMV in cell culture (31). For the construction of a recombination plasmid, a 4.75 kb SacI fragment (nucleotides 192648 to 197398 of the genome of the HCMV laboratory strain AD169; (3)) was cloned into the plasmid pGEM3Zf (Promega). Subsequently, a 2.7 kb NheI/PshAI fragment was deleted within the 4.75 kb SacI fragment and the gpt gene (under the control of the thymidine kinase promoter of the herpex simplex virus type 1 and followed by the polyA signal of SV40; (9, 11)) was inserted, as well as an oligonucleotide adapter with a PacI site (FIG. 13). Finally, the BAC vector pKSO (cf. Example 1) was inserted into the PacI site (FIG. 13). At its left side the recombination plasmid has 712 by and at its right side 1355 by of sequences homologous to the HCMV genome in the region of the US1 gene and US7 gene, respectively (cf. FIG. 13, center). Prior to electroporation the recombination plasmid was linearized with the enzyme XcmI in the region of the plasmid backbone.

About 30 µg of the linearized recombination plasmid was introduced by electroporation into human foreskin fibroblasts (HFF) (Biorad electroporator: 250 V, 960 pF). Approximately 24 hours after electroporation the HFF cells were infected with the HCMV laboratory strain AD169 at a moi of 1. After adsorption of the virus for four hours the cells were washed and new medium was added. Subsequently, the cells were further cultivated at 37° C. and with 5% $CO_2$ until a complete cytopathic effect was observed. The virus-containing cell culture supernatant was then transferred to new HFF cells and enriched with recombinant viruses by selection with mycophenolic acid (100 µM) and xanthine (25 µM) (9, 11). Upon achievement of a complete cytopathic effect the virus was again transferred to new HFF cells and subjected to a further selection round. After the 3rd selection round circular virus DNA was isolated from infected cells by the Hirt method (18; cf. Example 1) and introduced by eletroporation in *E. coli* DH10B as described in Example 2.

The unique-long (UL) region and the unique-short (US) region of the HCMV genome can change their orientation relative to one another by inversion at the internal and terminal repeats (open rectangles in FIG. 13) (3). After integration of the BAC vector at the expected position in the US region (cf. FIG. 13 bottom) two different isomeric forms of the HCMV-BAC genome are expected that can be distinguished by restriction digestion with HindIII (FIG. 14).

By plasmid isolation with subsequent HindIII restriction digestion, *E. coli* clones were identified that contained BAC plasmids with the HCMV genome, and HCMV-BAC plasmids with the two different isomeric forms were found (FIG. 15). Prototypes are the two BAC plasmids pHB5 and pHB8 (FIG. 15). pHB5 comprises HindIII fragments of 17.5 and 35 kb, whereas pHB8 with HindIII fragments of 22.1 and 30.3 kb shows the other orientation.

Transfection of pHB5 and pHB8 with Superfect (Qiagen, Hilden, Germany) into HFF cells and MRC5 fibroblasts resulted in the formation of plaques after about 10 to 14 days. The HCMV-BAC plasmids were transfected together with a plasmid which expresses the CMV protein pp 71 because it is known that pp 71 enhances the infectiousness of viral DNA (37). Per culture dish (6 cm diameter), 0.5-3 µg HCMV-BAC plasmid and 1 µg of the pp 71 expression plasmid were cotransfected. Viral DNA was isolated from cells infected with the pHB5 BAC virus and, for comparison, from cells infected with the HCMV laboratory strain AD169 (cf. Example 1), digested with EcoRI and separated on 0.5% agarose gels (FIG. 16). In comparison with the HCMV AD169 genome, the pHB5 genome lacks an 11.9 kb EcoRI fragment, but possesses new EcoRI fragments of 8.9, 5.8 and 2.0 kb (cf. FIG. 13; center and bottom).

The additional 2.0 kb EcoRI bands in the pHB5 genome can clearly be seen in FIG. 16. The additional 5.8 and 8.9 kb EcoRI bands and the absence of the 11.9 kb EcoRI band were confirmed by Southern blotting. Thus the pHB5 genome has the expected structure (cf. FIG. 16). The pHB8 genome was characterized in a similar way and also showed the expected structure.

After insertion of the BAC vector between the US1 and US7 genes the genome of the HCMV laboratory strain AD169 could be cloned as BAC plasmid in *E. coli*. Both isomeric forms to be expected were found. Infectious viruses could be reconstituted from both conformations after transfection in permissive human fibroblasts.

EXAMPLE 6

Mutagenesis of the HCMV-BAC Plasmid pHB5 and Production of HCMV Mutants

To demonstrate that HCMV mutants can be produced with the method, 380 by were deleted in exon 3 of the HCMV UL37 gene (3) and replaced by a 2.6 kb tetracycline cassette (32). For the mutagenesis the following recombination plasmid was constructed: a 9.7 kb BglII fragment from the HCMV AD169 genome (genome positions 47366-57120; 33, 3) was cloned into a pBluescript derivative (whose polylinker had previously been modified by insertion of an oligonucleotide and contained a BglII site). A 380 by SnaBI fragment was then excised from the 3rd exon of the UL37 gene and a 2.6 kb tetracycline cassette was inserted (cf. FIG. 17 "recombination plasmid"). Finally, the 8.9 kb BglII/DraI fragment was transferred into the BamHI/SmaI-cut shuttle plasmid pS'T76K_SacB (FIG. 18). The shuttle plasmid pST76K_SacB is a derivative of the plasmid pST76K (34). In addition to the kanamycin resistance gene and the temperature-sensitive replication mechanism, pST76K_SacB (FIG. 18) contains the negative selection marker SacB which allows a selection for the plasmid on agar plates with 5% saccharose.

Mutagenesis was similar to the method described in Example 2 (cf. FIG. 19). The HCMV-BAC plasmid pHB5 and the recombination shuttle plasmid were successively introduced by electroporation into *E. coli* CBTS (25). For the formation of cointegrates the clones were kept at 30° C. on agar plates with chloramphenicol (12.5 µg/ml) and kanamycin (50 µg/ml) because the CBTS strain expressed the recA protein essential for recombination only at 30° C. Clones in which cointegrates had formed were selected at 42° C. on agar plates with chloramphenicol (12.5 µg/ml) and kanamycin (50 µg/ml). The cointegrates were resolved by incubation of the bacterial clones at 30° C. on agar plates which only contained chloramphenicol (at 30° C. recA is expressed, see above). For identification of clones in which the cointegrate had been resolved, bacterial clones were streaked on agar plates with chloramphenicol (12.5 µg/ml) and 5% saccharose and incubated at 30° C. for 1.5-2 days. Bacteria which still contain the cointegrate and thus express the SacB protein cannot grow on such plates (negative selection), whereas this is possible for clones in which the cointegrate has been resolved. The resolution of the cointegrate was checked by testing for kanamycin sensitivity. The negative selection with the help of the SacB gene on saccharose-containing agar plates represents, as compared to the method described in Example 2, a considerable progress because clones in which the cointegrate has been resolved can be identified immediately.

Clones which contain the mutant BAC plasmid were finally identified because of their tetracycline resistance (incubation on plates with chloramphenicol (12.5 µg/ml) plus tetracycline (10 µg/ml)).

The BAC plasmid was isolated from one of the tetracycline-resistant clones, digested with EcoRI, and the cleavage pattern was compared with the EcoRI digestion of the start plasmid pHB5 (FIG. 20). The EcoRI cleavage pattern of the two BAC plasmids is identical, except for the expected changes, i.e. no changes took place outside the mutated region. As expected, a 6.38 kb band has disappeared in BAC plasmid pHB98/1. In return, there are two new EcoRI bands of 4.88 and 3.70 kb (see FIG. 20) because the inserted tetracycline cassette contains an additional EcoRI cleavage site (cf. FIG. 17 bottom).

The example shows that the HCMV-BAC plasmid can be mutated in a targeted manner and that the method is suited for producing mutant HCMV genomes.

The mutated HCMV-BAC plasmid pHB98/1 was transfected together with a pp 71 expression plasmid into MRC5 cells and led to the formation of plaques. The BAC plasmid pHB98/1 is thus infectious and, after transfection in permissive cells, leads to the formation of mutant viruses. Consequently, the UL37 gene is not essential for the replication of HCMV.

After mutagenesis the tetracycline cassette can again be deleted by expression of the FRT-specific FLP recombinase in the BAC-containing E. coli clone because the tetracycline cassette was only used for identifying the mutant clones more rapidly and easily. The use of the tetracycline cassette is not essential (cf. Example 2), but helpful under the said aspect. For deletion of the tetracycline cassette the plasmid pCP20 (32) was transformed in E. coli bacteria containing the BAC plasmid pHB98/1. pCP20 exhibits a temperature-sensitive replication mechanism and expresses the FLP recombinase (32). The excision of the tetracycline cassette was carried out during incubation of the E. coli bacteria at 30° C. Subsequently, the bacteria were streaked on agar plates with chloramphenicol (12.5 µg/ml) and incubated at 43° C. to lose the pCP20 plasmid again (32). Screening of the bacterial clones for tetracycline sensitivity revealed that the tetracycline cassette had been excised from the BAC plasmid in a majority of the clones. Isolation of the BAC plasmids and digestion with EcoRI revealed an additional 6.0 kb EcoRI band and the loss of the 3.7 and 4.88 kb EcoRI bands, thereby confirming the successful excision of the tetracycline cassette (see FIG. 17 bottom and FIG. 20, lane pHB/FLB).

EXAMPLE 7

Direct Transposon Mutagenesis of the Infectious MCMV-BAC Plasmid

Transposons are "jumping" genetic elements which are predominantly found in bacteria. As a rule, they contain the enzymes needed for transposition and one or several resistance genes. Modified transposons can be used for a randomized mutagenesis of bacterial genomes and plasmids. They insert at random sites into the DNA, thereby disrupting the open reading frame of the gene at the insertion site. This mutagenesis method was here used for the first time for the direct mutagenesis of BACs.

Based on the transposon TnMax8, a derivative of Tn1721 (35), the plasmid pST76A-TnMax8 was constructed. To this end pTnMax8 (which contains a kanamycin resistance gene) and the vector pST76-A (34) were linearized with the restriction enzyme PstI and fused by ligation to yield pST76A-TnMax8 (FIG. 21a). This plasmid has a temperature-sensitive replication mechanism enabling the same to replicate in E. coli at 30° C., but not at 42° C. For the direct transposon mutagenesis of the MCMV genome, DH5a bacteria were transformed with the MCMV-BAC and pST76A-TnMax8 and cultivated at 30° C. (FIG. 21b): A transposition of the transposon takes place after induction of the transposition enzymes, but also spontaneously. When these bacteria are streaked on an LB agar plate and incubated at 42° C. in the presence of chloramphenicol and kanamycin, only those bacteria in which a transposition has taken place and the kanamycin resistance has thereby been transferred will grow to colonies (FIG. 21b). Because of the temperature-sensitive replication mechanism, the plasmid pST76A-TnMax8 cannot replicate at 42° C. and is therefore lost. The MCMV-BAC plasmid replicates independently of the temperature, and selection for its absence is carried out with chloramphenicol. Since the Tn1721 derivatives appear preferably as negatively twisted plasmids, a transposition predominantly leads to insertion into the BAC and only seldom into the bacterial genome.

The characterization of an MCMV transposon mutant shall here by demonstrated in an exemplary manner with the clone MCMV-Kn5. To limit the insertion site of the transposon in the BAC, changes in the restriction pattern can be analyzed after restriction digestion (here with HindII) and gel electrophoresis. In the present case the disappearance of the 9.5 kb HindIII I band is observed as compared to the MCMV wild type (wt). It is subdivided by the transposon into two subfragments of about 6.4 and 3.1 kb (FIG. 22, FIG. 23a). In addition, a transposon-specific band of 1.8 kb can be seen in the HindIII digestion (FIG. 23a). By direct sequencing of the clone MCMV-Kn5 with primers which bind to the ends of the transposon, the insertion site could be localized approximately at the nucleotide position 198900 (FIG. 23b shows an alignment of the obtained sequence with the MCMV genome). This corresponds to an insertion into the gene m141 (FIG. 22).

Infectious virus was reconstituted by transfection of MCMV-Kn5 DNA into NIH-3T3 fibroblasts. In this virus the m141 gene is inactivated by insertion of the transposon. This could be demonstrated by restriction digestion of isolated virus DNA, with the same change as in FIG. 23a being observed. Thus it could be demonstrated at the same time that the gene m141 is not essential for the virus.

The above-described method has already been successfully applied to the mutagenesis of the cloned HCMV genome (data not shown). In addition to the transposon vector pST76A-TnMax8, further derivatives were constructed with tetracycline and erythromycin resistance genes. By sequential transposon mutagenesis mutants with two or three gene knockouts can be produced. Other transposons can also be used in a similar way for the direct mutagenesis of cloned virus genomes.

In addition, further functions can be inserted by changing the transposon used: for instance, the temporal expression of the knocked-out genes can be tracked by insertion of an indicator gene (e.g. IRES-EGFP). Virulence genes can also be identified in vivo by inserting sequence tags into the transposon (36).

EXAMPLE 8

Cloning of the Genome of the HCMV Strain Toledo as Bacterial Artificial Chromosome (BAC)

In comparison with the laboratory strain AD169 the HCMV strain Toledo has at least 19 additional genes (4). The strain Toledo is very similar to HCMV isolates from patients and is the prototype of a HCMV wild-type strain (4). It was therefore important to show that genome sequences from an HCMV isolate from a patient are also suited for producing the recombinant vector according to the invention.

For the production of the Toledo-BAC plasmid, use was made of the recombination plasmid described in Example 5. As described in Example 5, about 30 µg of the XcmI-linearized recombination plasmid was introduced by electroporation into human foreskin fibroblasts. About 24 hours after electroporation the HFF cells were infected with the HCMV strain Toledo at a moi of 1. The enrichment method with mycophenolic acid and xanthine was carried out as described in Example 5. Finally, circular virus DNA was isolated from the infected HFF cells and introduced by electroporation into *E. coli* DH10B. Then plasmid DNA was isolated from several bacterial clones, digested with EcoRI, and the cleavage pattern was compared with the EcoRI cleavage pattern of the Toledo virus DNA (FIG. 24). The cleavage pattern of the BAC clones is largely identical with that of the Toledo virus DNA, i.e. the BAC plasmids contain the complete Toledo genome except for the integration site of the BAC vector in the US2-US6 region. The EcoRI pattern of the various BAC plasmids shows small differences in individual fragments in the region between about 9.5 and 13 kb. This polymorphism is explained, on the one hand, by the different isomeric forms of the HCMV Toledo genome (cf. Example 5 and FIG. 14); on the other hand, the number of a-repeats can also vary (3), whereby the length of individual EcoRI fragments changes. FIG. 25 shows the HindIII and XbaI cleavage patterns of some Toledo-BAC plasmids. These patterns are also identical except for the size of a few fragments.

The example shows that the method for producing the recombinant vector according to the invention is suited for cloning genome sequences of various HCMV strains, including HCMV isolates from patients.

Literature:
1. Britt, W. J. & Alford, C. A. (1996) in: *Fields* Virology, eds. Fields, B. N., Knipe, D. M. & Howley, P. M. (Lippincott-Raven, New York), pp. 2493-2523.
2. Ho, M. (1991) in: *Cytomegalovirus*: biology and infection, ed. Ho, M. (Plenum Publishing Corp., New York).
3. Chee, M. S., Bankier, A. T., Beck, S., Bohni, R., Brown, C. M., Cerny, R., Horsnell, T., Hutchison, C. A., Kouzarides, T., Martignetti, J. A., Preddie, E., Satchwell, S. C., Tomlinson, P., Weston, K. M. & Barrell, B. G. (1990) *Curr. Top. Microbiol. Immunol.* 154, 125-169.
4. Cha, T.-A., Tom, B., Kembie, G. W, Duke, G. M., Mocarski, E. S. & Spate, R. R. (1996) *J. Virol.* 70, 78-83.
5. Rawlinson, W. D., Farrell, H. E. & Barrell, B. G. (1996) *J. Virol.* 70, 8833-8849.
6. Roizman, B. & Sears, A. E. (1996) in: *Fields* Virology, eds. Fields, B. N., Knipe, D. M. & Howley, P. M. (Lippincott-Raven, New York), pp. 2231-2295.
7. Spaete, R. & Mocarski, E. S. (1987) *Proc. Natl. Acad. Sci. USA* 84, 7213-7217.
8. Manning, W. C. & Mocarski, E. S. (1988) *Virology* 167, 477-484.
9. Vieira, J., Farrell, H. E., Rawlinson, W. D. & Mocarski, E. S. (1994) *J. Virol.* 68, 4837-4846.
10. Wolff, D., Jahn, G. & Plachter, B. (1993) *Gene* 130, 167-173.
11. Greaves, R. F., Brown, J. M., Vieira, J. & Mocarski, E. S. (1995) *J. Gen. Virol.* 76, 2151-2160.
12. van Zijl, M., Quint, W., Briaire, J., de Rover, T., Gielkens, A. & Berns, A. (1988) *J. Virol.* 62, 2191-2195.
13. Kemble, G., Duke, G., Winter, R. & Spaete, R. (1996) *J. Virol.* 70, 2044-2048.
14. Ebeling, A., Keil, G. M., Knust, E. & Koszinowski, U. H. (1983) *J. Virol.* 47, 421-433.
15. Thale, R., Szepan, U., Hengel, H., Geginat, G., Lucin, P. & Koszinowski U. H. (1995) *J. Virol.* 69, 6098-6105.
16. Messerle, M., BUhler, B. Keil, G. M. & Koszinowski, U. H. (1992) *J. Virol.* 66, 27-36.
17. Mercer, J. A., Marks, J. R. & Spector, D. H. (1983) *Virology* 129, 94-106.
18. Hirt, B. (1967) *J. Mol. Biol.* 26, 365-369.
19. Shizuya, H., Birren, B., Kim, U. J., Mancino, V., Slepak, T., Tachiiri, Y. & Simon, M. (1992). *Proc. Natl. Acad. Sci. USA* 89, 8794-8797.
20. Maniatis, T., Fritsch, E. F. & Sambrook, J. (1989) *Molecular Cloning: A Laboratory Manual*. (Cold Spring Harbor Lab. Press, Plainview, N.Y.).
21. Chang, A. C. & Cohen, S. N. (1978) *J. Bacteriol.* 134, 1141-56.
22. Sauer, B. (1993) *Methods Enzymol.* 225, 890-900.
23. Keil, G. M., Ebeling-Keil, A. & Koszinowski, U. H. (1987) *J. Virol.* 56, 526-533.
24. O'Connor, M., Peifer, M. & Bender, W. (1989) *Science* 244, 1307-1312.
25. Kempkes, B., Pich, D., Zeidler, R., Sugden, B. & Hammerschmidt, W. (1995) *J. Virol.* 69, 231-238.
26. Mocarski, E. S. (1996) in: *Fields Virology*, eds Fields, B. N., Knipe, D. M. & Howley, P. M. (Lippincott-Raven, New York), pp. 2447-2492.
27. Pfüller, R. & Hammerschmidt, W. (1996) *J. Virol.* 70, 3423-3431.
28. Del Val, M., Volkmer, H., Rothbard, J. B., Jonjic, S., Messerle, M., Schickedanz, J., Reddehase, M. J. & Koszinowski, U. H. (1988) *J. Virol.* 62, 3965-3972.
29. Virgin, H. W. 4th, Latreille, P., Wamsley, P., Hallsworth-K; Weck, K. E., Dal Canto, A. J., Speck, S. H. (1997) *J. Virol.* 71, 5894-5904.
30. Simas, J. P., Bowden, R. J., Paige, V., Efstathiou, S. (1998) *J. Gen. Virol.* 79, 149-153.
31. Jones, T. R., Hanson, K, Sun, L., Slater, J. S., Stenberg, R. M., Campbell, A. E. (1995) *J. Virol.* 69, 4830-4841.
32. Cherepanov, P. P., Wackernagel, W. (1995) *Gene* 158, 9-14.
33. Dargan, D. J., Jamieson, F. E., MacLean, J., Dolan, A., Addison, C., McGeoch, D. J. (1997) *J. Virol.* 71, 9833-9836.
34. Posfai, G, Koob, M. D., Kirkpatrick, H. A., Blattner, F. R. (1997) *J. Bacteriol.* 179, 4426-4428.
35. Kahrs, A. F., Odenbreit, S., Schmitt, W., Heuermann, D., Meyer T. F., Haas, R. (1995) *Gene* 167:53-57.
36. Hensel, M., Shea, J. E., Gleeson, C., Jones, M. D., Dalton, E., Holden, D. W. (1995) *Science* 269:400-403.
37. Baldick, C. J. Jr., Marchini, A., Patterson, C. E., Shenk, T. (1997) *J. Virol.* 71:4400-4408.

The invention claimed is:

1. A bacterial artificial chromosome (BAC) containing bacterial nucleic acid sequences and an infectious herpes virus genomic sequence larger than 100 kb, wherein the BAC contains all genes that are essential for the generation of an infectious herpes virus in a host cell, and wherein the host cell does not contain any herpes virus genes or herpes virus proteins.

2. The BAC of claim 1, wherein the infectious herpes virus genomic sequence is larger than 200 kb.

3. The BAC of claim 1, wherein said herpes virus is a beta herpes virus.

4. The BAC of claim 3, wherein said beta herpes virus is a human cytomegalovirus.

5. The BAC of claim 3, wherein said beta herpes virus is a mouse cytomegalovirus.

6. The BAC of claim 1, wherein said herpes virus is a gamma herpes virus.

7. The BAC of claim 6, wherein said gamma herpes virus is murine gamma herpes virus 68 (MHV 68).

8. The BAC of claim 1, wherein the bacterial nucleic acid sequences are flanked by nucleotide sequences which are identical to each other and which, upon homologous recombination, enable excision of the bacterial nucleic acid sequences.

9. The BAC of claim 1, wherein the bacterial nucleic acid sequences are flanked by (i) recognition sequences for sequence-specific recombinases, (ii) unique restriction enzyme sites, or (iii) recognition sequences for sequence-specific recombinases and unique restriction enzyme sites.

10. The BAC of claim 9, wherein the recognition sequences are loxP sites.

11. The BAC of claim 1, which further contains (i) a selection gene, (ii) a marker gene, or (iii) a selection gene and a marker gene.

12. The BAC of claim 8, which further contains (i) a selection gene, (ii) a marker gene, or (iii) a selection gene and a marker gene.

13. The BAC of claim 9, which further contains (i) a selection gene, (ii) a marker gene, or (iii) a selection gene and a marker gene.

14. An isolated cell containing the BAC of claim 1.

15. An isolated cell containing the BAC of claim 8.

16. An isolated cell containing the BAC of claim 9.

17. An isolated cell containing the BAC of claim 11.

18. An isolated cell containing the BAC of claim 12.

19. An isolated cell containing the BAC of claim 13.

20. A method of producing the BAC of claim 1, which method comprises:

(a) introducing bacterial nucleic acid sequences into a host cell containing infectious herpes virus genomic sequences, and (b) recombining the bacterial nucleic acid sequences with the infectious herpes virus genomic sequences, whereupon the BAC is obtained.

21. The method of claim 20, wherein step (b) is carried out by homologous recombination.

22. The method of claim 20, wherein said host cell is a eukaryotic cell.

23. The method of claim 22, wherein said eukaryotic cell is a mammalian cell.

24. The method of claim 23, wherein said mammalian cell is a primary fibroblast, a human foreskin fibroblast (HFF), or a mouse embryonic fibroblast.

25. The method of claim 24, wherein said primary fibroblast is an NIH3T3 fibroblast.

26. The method of claim 20, wherein said bacterial nucleic acid sequences are introduced into the host cell by calcium phosphate precipitation, lipofection or electroporation.

27. The method of claim 20, wherein said bacterial nucleic acid sequences are introduced into the host cell by a viral vector.

28. The method of claim 20, wherein said host cell is a bacterial organism.

29. The method of claim 28, wherein said bacterial organism is *Escherichia coli*.

30. A method of mutagenizing the infectious herpes virus genomic sequence in the BAC of claim 1, which method comprises: (a) introducing the BAC of claim 1 into a bacterial host cell, (b) exposing the BAC to mutagenizing DNA molecules, whereupon the infectious herpes virus genomic sequence in the BAC is mutagenized.

31. The method of claim 30, wherein step (b) is carried out by homologous recombination between the BAC and the mutagenizing DNA molecules.

32. The method of claim 31, wherein there is a mutant allele in the mutagenizing DNA molecules and homologous recombination is carried out between the infectious herpes virus genomic sequence and the mutant allele.

33. The method of claim 30, wherein there is a transposon in the mutagenizing DNA molecules and step (b) is carried out by the transposon.

* * * * *